United States Patent
Scholler et al.

(10) Patent No.: US 10,160,809 B2
(45) Date of Patent: Dec. 25, 2018

(54) ANTI-TEM1 ANTIBODIES AND USES THEREOF

(71) Applicant: THE TRUSTEES OF THE UNIVERSITY OF PENNSYLVANIA, Philadelphia, PA (US)

(72) Inventors: Nathalie Scholler, Penn Valley, PA (US); Aizhi Zhao, Drexel Hill, PA (US); Donald Siegel, Lansdale, PA (US); George Coukos, Vaud (CH)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 147 days.

(21) Appl. No.: 15/411,938

(22) Filed: Jan. 20, 2017

(65) Prior Publication Data

US 2017/0281793 A1  Oct. 5, 2017

Related U.S. Application Data

(62) Division of application No. 13/508,925, filed as application No. PCT/US2010/056477 on Nov. 12, 2010, now Pat. No. 9,556,272.

(60) Provisional application No. 61/260,286, filed on Nov. 11, 2009.

(51) Int. Cl.
| | |
|---|---|
| *C07K 16/18* | (2006.01) |
| *A61K 51/10* | (2006.01) |
| *A61K 39/395* | (2006.01) |
| *A61P 39/00* | (2006.01) |
| *A61K 39/44* | (2006.01) |
| *C07K 16/28* | (2006.01) |
| *G01N 33/574* | (2006.01) |
| *A61K 47/68* | (2017.01) |
| *A61K 39/00* | (2006.01) |

(52) U.S. Cl.
CPC ...... *C07K 16/2851* (2013.01); *A61K 47/6849* (2017.08); *A61K 2039/505* (2013.01); *C07K 2317/21* (2013.01); *C07K 2317/622* (2013.01); *C07K 2317/77* (2013.01); *C07K 2317/92* (2013.01)

(58) Field of Classification Search
None
See application file for complete search history.

*Primary Examiner* — Julie Wu
(74) *Attorney, Agent, or Firm* — Mark S. Cohen; Pearl Cohen Zedek Latzer Baratz LLP

(57) ABSTRACT

The invention relates to Anti-TEM 1 antibodies or antigen-binding fragments thereof, yeast libraries comprising the same, and prophylactic, diagnostic, and therapeutic methods using the same.

5 Claims, 12 Drawing Sheets

Specification includes a Sequence Listing.

ANTI-TEM1 ANTIBODIES AND USES THEREOF

CROSS-REFERENCE TO RELATED APPLICATIONS

This application is a Divisional of U.S. patent application Ser. No. 13/508,925, filed on Aug. 1, 2012 which is a National Phase Application of PCT International Application No. PCT/US10/56477, International Filing Date Nov. 12, 2010, claiming priority to U.S. Provisional Patent Application 61/260,286, filed Nov. 11, 2009, each of which is incorporated by reference herein in its entirety.

GOVERNMENT INTEREST

The work described in this patent application was supported, in part, by the Institute for the Translational Medicine and Therapeutics (CA016520/NIH) (NS), and the National Heart, Lung, and Blood Institute (P50-HL81012) (DLS). The Unites States government may have certain rights in this patent application.

FIELD OF THE INVENTION

The invention relates to an antibody or antigen-binding fragment that binds specifically to an endosialin tumor endothelial marker 1 (TEM1), and prophylactic, diagnostic, and therapeutic methods using the same.

BACKGROUND OF THE INVENTION

Isolation of antigen-specific antibodies has been achieved through a variety of methods, including screening of phage-display recombinant antibody (scFv) libraries. Yeast-display recently emerged as an efficient alternative strategy for scFv identification that offers several advantages over prokaryotic systems, including superior sampling of the immune antibody repertoire; post-translational modifications (glycosylation) due to the eukaryotic expression; faster and more controlled flow cytometry-based selection compared to solid phase panning; and absence of growth bias, as recombinant proteins are displayed at the yeast cell surface only during the induction step in the presence of galactose. Yet, previously reported yeast libraries have been severely limited in size, with typically less than $1 \times 10^5$ transformants per microgram of DNA for commonly used strains, resulting in insufficient diversity and potential for yielding high affinity antibodies. Additionally, with existing methods, transfer of scFv from displayed to secreted forms has often resulted in loss of antigen specificity and/or affinity, requiring additional time-consuming and costly steps, including in vitro maturation of scFv sequence and/or recloning of scFv fused to immunoglobulin (Ig) constant regions. The mechanisms underlying loss of scFv function include changes in scFv conformation and post-translational modification due to different expression systems for displayed and secreted forms.

It was hypothesized that the use of electroporation combined with buffer modifications could remove obstacles contributed by poor yeast transformation efficiency. In addition, we hypothesized that only one expression system (Saccharomyces cerevisiae) for both scFv display and secretion could eliminate changes in scFv post-translational modifications, while keeping the advantages of an eukaryotic system for the expression of high-affinity antibodies. It was also hypothesized that if both displayed and secreted scFv were modified only at the N-terminus, which binds to the yeast surface or to secondary reagents, respectively, conformational changes would be minimized during the shift from displayed to secreted forms. To test this hypotheses, a previously generated M13 bacteriophage display human scFv library was transferred through homologous recombination into our novel vector pAGA2 for yeast-display. This yielded a $1 \times 10^9$-member yeast scFv display library, which was then screened in two steps using two novel complementary yeast systems. The first was engineered to permit scFv surface expression as a fusion with an Aga2 protein to N-termini for convenient high-throughput screening by flow sorting. The second was engineered to permit rapid transformation into yeast-secreted soluble scFvs fused to N-termini to an IgA hinge and an enzymatically biotinylatable site for in vitro and in vivo validation. Such scFv are called "biobodies" after targeted biotinylation by yeast mating. As proof of principle, we used this novel platform to screen for scFv against the tumor marker endosialin/tumor endothelial marker 1 (TEM1) or CD248, an attractive target for antibody-based tumor diagnosis and therapy. Several high-affinity TEM1-specific yeast-secreted scFvs and biobodies were isolated and characterized for binding to human and murine TEM1 in vitro and in vivo. The highest affinity anti-TEM1 biobody-78 (Kd 4 nM) was able to bind both murine and human TEM1 and selectively targeted TEM1-expressing tumor cells in a novel in vivo mouse model of orthotopic ovarian cancer. This streamlined approach for rapid identification of high affinity reagents suitable for in vivo use paves the way for the high throughput development of novel antigen-targeted theranostics.

SUMMARY OF THE INVENTION

In one embodiment, the invention provides an isolated antibody or antigen-binding fragment, whereby said antibody or antigen-binding fragment is, in another embodiment, specific for both the mouse and human form of an endosialin tumor endothelial marker 1 (TEM1).

In another embodiment, the invention provides a method of treating a tumor in a subject comprising the step of contacting said tumor cell with said antibody or antigen-binding fragment thereof of that is operably linked to a biologically active agent, wherein said agent is a toxin, a radioisotope, a nanoparticle or a bio-active peptide.

In another embodiment, the invention provides a method of treating angiogenesis of a solid tumor in a subject, said method comprising the step of contacting a pericyte of said solid tumor with said antibody or antigen-binding fragment thereof of is operably linked to a biologically active agent, wherein said agent is a toxin, a radioisotope, a nanoparticle or a bio-active peptide.

In another embodiment, the invention provides a method of diagnosing the presence of a tumor or a cancer growth in a subject, said method comprising sampling a tissue sample isolated from said subject with a composition comprising said antibody or antigen-binding fragment, whereby specific binding of said antibody or antigen-binding fragment to said tissue sample is indicative of the presence of a tumor or cancer growth in said subject.

In another embodiment, the invention provides a method of imaging a TEM1-containing tumor, said method comprising the step of applying said antibody or antigen-binding fragment operably linked to a secondary reagent; whereby said secondary reagent can be visualized once said antibody or antigen-binding fragment has bound its target TEM1.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 5: Germline immunoglobulin gene usage and predicted amino acid sequences of anti-TEM1 scFv a. Anti-TEM1 heavy chain variable regions. The number of nucleotide differences from germline $V_H$ is tabulated to the right of each sequence. In general, D segments showed very poor homology with known D genes so mutations were not scored in these regions. FR (framework region) and CDR (complementarily determining region) designations as per Kabat. b. Anti-TEM1 light chain variable regions. The number of nucleotide differences from germline $V_L$ is tabulated to the right of each sequence.

FIG. 10: Biodistribution of anti-TEM1 biobodies. Mice were first implanted in the left bursa with MOV1 cells, IV-injected three weeks later with anti-TEM1 biobody-78 (a-j) or biobody-137 (k-o), and sacrificed 24 (a-e) or 48 hours (f-o) later. Bindings of anti-TEM1 biobodies to the left ovary (a,f,k), right ovary (b,g,l), spleen (c,h,m), liver (d, i, n) and kidney (e, j, o) were assessed by confocal microscopy (63×) by staining with 1 μg/ml of rhodamine-conjugated streptavidin (2). Presence of tumor cells was detected with 2 μg/ml of anti-SV40 mAb followed by 1 μg/ml of alexa-488 goat anti-mouse IgG2a (1). DAPI staining to visualized nuclei (3). (4) Merged images of (1), (2) and (3).

DETAILED DESCRIPTION OF THE INVENTION

Figure 1:
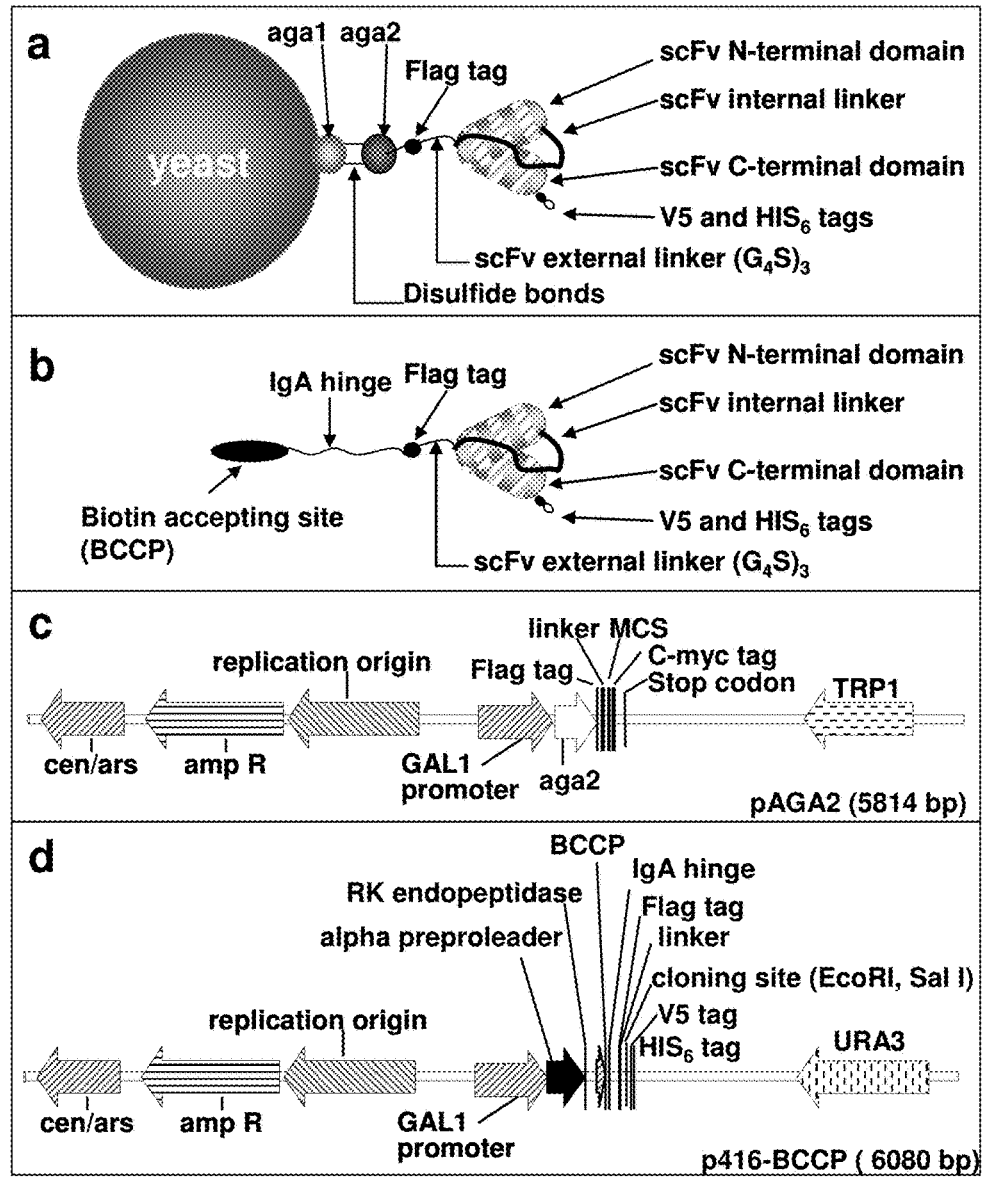
FIG. 1. Companion vectors for yeast-display and yeast-secreted scFv expression. a-b: Overall structures of yeast-display (a) and yeast-secreted scFv (b). c: pAGA2 vector for yeast-display. The shuttle vector p414 GAL1 that allows galactose-inducible expression in presence of uracil was modified to include Nhe1, EcoR1 and Xho1 restriction enzyme sites matching the cloning sites of its companion vector p416 BCCP (d). The multiple cloning site (MCS) was engineered by inserting a Nhe1 site after the FLAG tag and $(G_4S)_3$ linker sequence; an EcoR1 site, also part of a stop codon that is removed when cDNA are inserted in frame in the cloning site; and a Xho1 site, inserted directly before the c-myc tag, out of frame with the FLAG tag, to insure that both tags would be expressed only in presence of correctly inserted cDNA. d: p416-BCCP for yeast-secretion. The shuttle vector p416 GAL1 that allows for galactose-inducible secretion in the presence of tryptophane was linearized by BamH1 and Xho1 and co-transformed in yeast with a purified PCR product encoding alpha preproleader and RK endopeptidase sequences followed by biotin accepting site (BCCP), IgA hinge, FLAG tag, $(G_4S)_3$ linker, cloning site with stop codon, and V5-HIS tags.

This invention relates in one embodiment to isolated antibodies or antigen-binding fragments thereof that selectively bind the same human and mouse target, methods of treatment comprising administering said antibodies or antigen-binding fragments, and yeast libraries comprising said antibodies or antigen-binding fragments in display or secretable forms. In one embodiment, provided herein is an isolated antibody or antigen-binding fragment that is specific for both the mouse and human form of an endosialin tumor endothelial marker 1 (TEM1). In another embodiment, the antibody or antigen-binding to fragment binds the TEM1 epitope exemplified herein (see Examples). In another embodiment, the antibody or antigen-binding fragment binds the TEM1 epitope sequence set forth in SEQ ID NO: 40, provided herein below.

In some embodiments, the term "epitope" refers to a region of the antigen that binds to the antibody. It is the region of an antigen recognized by a first antibody wherein the binding of the first antibody to the region prevents binding of a second antibody or other bivalent molecule to the region. The region encompasses a particular core sequence or sequences selectively recognized by a class of antibodies. In general, epitopes are comprised by local surface structures that can be formed by contiguous or noncontiguous amino acid sequences.

In another embodiment, the term "Selectively recognizes", "selectively bind" or "selectively recognized" means that binding of the antibody or other bivalent molecule to an epitope is at least 2-fold greater, preferably 2-5 fold greater, and most preferably more than 5-fold greater than the binding of the bivalent molecule to an unrelated epitope or than the binding of an unrelated bivalent molecule to the epitope, as determined by techniques known in the art and described herein, such as, for example, ELISA and cold displacement assays.

In some embodiments, the term "antibody" refers to the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

In some embodiments, the term "antibody" or "antigen-binding fragment" respectively refer to intact molecules as well as functional fragments thereof, such as Fab, a scFv-Fc bivalent molecule, F(ab')$_2$, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

(6) scFv-Fc, is produced in one embodiment, by fusing single-chain Fv (scFv) with a hinge region from an immunoglobulin (Ig) such as an IgG, and Fc regions.

In one embodiment, the antibody provided herein is a monoclonal antibody. In another embodiment, the antigen-binding fragment provided herein is a single chain Fv (scFv), a diabody, a tandem scFv, a scFv-Fc bivalent molecule, an Fab, Fab', Fv, or F(ab')$_2$.

In one embodiment, the term "Bivalent molecule" or "BV" refers to a molecule capable of binding to two separate targets at the same time. The bivalent molecule is not limited to having two and only two binding domains and can be a polyvalent molecule or a molecule comprised of linked monovalent molecules. The binding domains of the bivalent molecule can selectively recognize the same epitope or different epitopes located on the same target or located on a target that originates from different species. The binding domains can be linked in any of a number of ways including, but not limited to, disulfide bonds, peptide bridging, amide bonds, and other natural or synthetic linkages known in the art (Spatola et al., "Chemistry and Biochemistry of Amino Acids, Peptides and Proteins," B. Weinstein, eds., Marcel Dekker, New York, p. 267 (1983) (general review); Morley, J. S., "Trends Pharm Sci" (1980) pp. 463-468 (general review); Hudson et al., Int J Pept Prot Res (1979) 14, 177-185; Spatola et al., Life Sci (1986) 38, 1243-1249; Hann, M. M., J Chem Soc Perkin Trans I (1982) 307-314; Almquist et al., J Med Chem (1980) 23, 1392-1398; Jennings-White et al., Tetrahedron Lett (1982) 23, 2533; Szelke et al., European Application EP 45665; Chemical Abstracts 97, 39405 (1982); Holladay, et al., Tetrahedron Lett (1983) 24, 4401-4404; and Hruby, V. J., Life Sci (1982) 31, 189-199).

In another embodiment, the antigen-binding fragment thereof is high affinity anti-TEM1 scFv-78. In another embodiment, the antigen-binding fragment thereof is low affinity anti-TEM1 scFv-137. In another embodiment scFv78 specifically binds the highly conserved fragment of the mouse and human TEM1 proteins comprising amino acids 324 to 390 where and in other embodiments, said fragment is the T6 fragment of the TEM1 protein located in the middle of the extracellular domain.

In one embodiment, the term "binds" or "binding" or grammatical equivalents, refers to the compositions having affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In one embodiment, the antibody or antigen binding fragment binds its target with a Kd within the 0.1 nM range.

In one embodiment, the antibody or antigen-binding fragment thereof provided herein comprises a modification. In another embodiment, the modification minimizes conformational changes during the shift from displayed to secreted forms of the antibody or antigen-binding fragment. It is to be understood by a skilled artisan that the modification can be a modification known in the art to impart a functional property that would not otherwise be present if it were not for the presence of the modification. The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

In another

In another embodiment, the modification is one as further defined herein below. In some embodiments, the modification is a N-terminus modification. In another embodiment, the modification is a C-terminal modification. In yet another embodiment, the modification is an N-terminus biotinylation. In yet another embodiment, the modification is an C-terminus biotinylation. In one embodiment, the secretable form of the antibody or antigen-binding fragment comprises an N-terminal modification that allows binding to an Immunoglobulin (Ig) hinge region. In another embodiment, the Ig hinge region is from but is not limited to, an IgA hinge region. In another embodiment, the secretable form of the antibody or antigen-binding fragment comprises an N-terminal modification that allows binding to an enzymatically biotinylatable site. In another embodiment, the secretable form of the antibody or antigen-binding fragment comprises an C-terminal modification that allows binding to an enzymatically biotinylatable site. In another embodiment biotinylation of said site functionilizes the site to bind to any surface coated with streptavidin, avidin, avidin-derived moieties, or a secondary reagent.

In another embodiment, the secondary reagent is a protein, a peptide, a carbohydrate, or a glycoprotein.

In one embodiment, biotinylating scFv-78 at the N-terminus generates biobody-78. In another embodiment, biobody-78 strongly binds to cell lines transduced with human TEM1 and cells that express high and moderate levels of endogenous human or mouse TEM1. In another embodiment, biotinylating said scFv-137 at the N-terminus generates biobody-137.

In another embodiment, an N-terminal modification of the antibody or antigen-binding fragment provided herein allows fusion of the antibody or antigen-binding fragment with a glycoprotein on the surface of a yeast cell. In another embodiment, the glycoprotein is a protein involved in yeast mating. In yet another embodiment, the glycoprotein is one involved in ligand/receptor interactions. In another embodiment, the glycoprotein includes but is not limited to an Aga2. In another embodiment, the antibodies or antigen-binding fragments from the yeast-display library are not biotinylated. In another embodiment, antibodies or antigen-binding fragments from the yeast-display are attached to a yeast surface via a glycoprotein. In yet another embodiment, the glycoprotein is an Aga2 or any glycoprotein known in the art to be useful for binding said antibodies or antigen-binding fragments to a yeast surface.

In one embodiment, an "isolated peptide" or "polypeptide" refers to an antibody or antigen-binding fragment as further provided herein. In another embodiment, when in reference to any polypeptide of this invention, the term is meant to include native polypeptides (either degradation products, synthetically synthesized peptides or recombinant peptides) and peptidomimetics (typically, synthetically synthesized peptides), such as peptoids and semipeptoids which are peptide analogs, which may have, for example, modifications rendering the polypeptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C A Ramsden Gd., Chapter 17.2, F. Choplin Pergamon Press (1992). In one embodiment, a polypeptide is a full length protein or a variant of a known protein.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression.

In one embodiment, the term "polypeptide" generally refers to the antibody, antigen-binding fragments or variants of the present invention.

In one embodiment, the polypeptide of this invention comprises an amino acid substitution. In one embodiment, the amino acid substitution is conservative. A "conservative amino acid substitution" is one in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In another embodiment, the amino acid substitution is not a conservative one that results in enhanced activity of the mutated polypeptide compared to the native polypeptide.

The antibodies or antigen-binding fragments of this invention can be produced by any synthetic or recombinant process such as is well known in the art. The antibodies or antigen-binding fragments of the invention can further be modified to alter biophysical or biological properties by means of techniques known in the art. For example, the polypeptide can be modified to increase its stability against proteases, or to modify its lipophilicity, solubility, or binding affinity to its native receptor.

In some embodiments, antibody fragments may be prepared by proteolytic hydrolysis of the antibody or by expression in *E. coli* or mammalian cells (e.g. Chinese hamster ovary cell culture or other protein expression systems) of DNA encoding the fragment. Antibody fragments can, in some embodiments, be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

A "variant" of a polypeptide, antibody, or protein of the present invention, in one embodiment, refers to an amino acid sequence that is altered with respect to the referenced polypeptide, antibody, or protein by one or more amino acids. In the present invention, a variant of a polypeptide retains the antibody-binding property of the referenced protein. In another embodiment, a "variant" refers to the antigen-binding framgent of the present invention. In yet another embodiment, the variant is a variant of the antigen-binding fragment that retains specificity for a target or marker. The variant may have "conservative" changes, wherein a substituted amino acid has similar structural or chemical properties (e.g., replacement of leucine with isoleucine). In another embodiment, the variants have conservative amino acid substitutions at one or more predicted non-essential amino acid residues. In another embodiment, a "conservative amino acid substitution" is one in which the amino acid residue is replaced with an amino acid residue having a side chain with a similar charge, where, in other embodiments, the opposite is the case for "non-conservative substitutions". Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein may routinely be expressed and the functional and/or biological activity of the encoded protein, can be determined using techniques described herein or by routinely modifying techniques known in the art. Analogous minor variations may also include amino acid deletions or insertions, or both. Guidance in determining which amino acid residues may be substituted, inserted, or deleted without abolishing immunological reactivity may be found using computer programs well known in the art, for example, DNASTAR software.

In one embodiment, the antibody or antigen-binding fragment provided herein has a mutation in the light chain (VL). In another embodiment, the mutation is a conservative mutation. In another embodiment, the mutation is a non-conservative one. In another embodiment, the mutation present in the VL chain is a serine to leucine point mutation in framework region (FR) 1. In another embodiment, the mutation present in the VL chain of the antigen-binding fragment is a glycine to valine point mutation in framework region 3. In another embodiment, the mutation present in the VL chain of the antigen-binding fragment is a leucine to methionine mutation in the complementarity determining region (CDR) 2.

In one embodiment, the term "framework region" or "FR" are those variable domain residues other than the hypervariable region residues. The framework regions have been precisely defined. See, e.g., Kabat, E. A. et al., Sequences of Proteins of Immunological Interest, US Dept. Health and Human Services, National Institutes of Health, USA (5th ed. 1991). Each variable domain typically has four FRs identified as FR1, FR2, FR3 and FR4. In some embodiments, "FR" also refers to an antibody variable region comprising amino acid residues abutting or proximal to, but outside of the CDR regions i.e. regions which directly interact with the antigen, acting as the recognition element of the antibody molecule within the variable region of an antibody. In one embodiment, the term "framework region" is intended to mean each domain of the framework that is separated by the CDRs. In some embodiments, the sequences of the framework regions of different light or heavy chains are relatively conserved within a species. The combined heavy and light chain framework regions of an antibody serve to position and align the CDRs for proper binding to the antigen.

In one embodiment, the term "CDR" or "complementarity determining region" refers amino acid residues comprising non-contiguous antigen combining sites found within the variable region of both heavy and light chain polypeptides. In other embodiments, the term "CDR" will comprise regions as described by Kabat et al., J. Biol. Chem. 252, 6609-6616 (1977) and Kabat et al., *Sequences of protein of immunological interest*. (1991), and Chothia and Lesk, *J. Mol. Biol.* 196:901-917 (1987) and MacCallum et al., *J. Mol. Biol.* 262:732-745 (1996). The amino acids of the CDRs of the variable domains were initially defined by Kabat, based on sequence variability, to consist of amino acid residues 31-35B (H1), 50-65 (H2), and 95-102 (H3) in the human heavy chain variable domain (VH) and amino acid residues 24-34 (L1), 50-56 (L2), and 89-97 (L3) in the human light chain variable domain (VL), using Kabat's numbering system for amino acid residues of an antibody. See Kabat et al., sequences of proteins of immunological interest, US Dept. Health and Human Services, NIH, USA (5th ed. 1991). Chothia and Lesk, J. Mol. Biol. 196:901-917 (1987) presented another definition of the CDRs based on residues that included in the three-dimensional structural loops of the variable domain regions, which were found to be important in antigen binding activity. Chothia et al. defined the CDRs as consisting of amino acid residues 26-32 (H1), 52-56 (H2), and 95-102 (H3) in the human heavy chain variable domain (VH), and amino acid residues 24-34 (L1), 50-56 (L2), and 89-97 (L3) in the human light chain variable domain (VL). Combining the CDR definitions of Kabat and Chothia, the CDRs consist of amino acid residues 26-35B (H1), 50-65 (H2), and 95-102 (H3) in human VH and amino acid residues 24-34 (L1), 50-56 (L2), and 89-97 (L3) in human VL, based on Kabat's numbering system.

In some embodiments, a "variable region" when used in reference to an antibody or a heavy or light chain thereof is intended to mean the amino terminal portion of an antibody which confers antigen binding onto the molecule and which is not the constant region. The term is intended to include functional fragments thereof which maintain some of all of the binding function of the whole variable region. Therefore, the term "heteromeric variable region binding fragments" is intended to mean at least one heavy chain variable region and at least one light chain variable regions or functional fragments thereof assembled into a heteromeric complex. Heteromeric variable region binding fragments include, for example, functional fragments such as Fab, F(ab)$_2$, Fv, single chain Fv (scfv) and the like. Such functional fragments are well known to those skilled in the art. Accordingly, the use of these terms in describing functional fragments of a heteromeric variable region is intended to correspond to the definitions well known to those skilled in the art. Such terms are described in, for example, Harlow and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Plückthun and Skerra, Meth. Enzymol., 178:497-515 (1989) and in Day, E. D., Advanced Immunochemistry, Second Ed., Wiley-Liss, Inc., New York, N.Y. (1990).

In one embodiment the polypeptide of this invention is an isoform of the isolated polypeptide. In one embodiment, "isoform" refers to a version of a molecule, for example, a protein or polypeptide of the present invention, with only slight differences to another isoform of the same protein or polypeptide. In one embodiment, isoforms are produced from different but related genes, or in another embodiment, arise from the same gene by alternative splicing. In another embodiment, isoforms are caused by single nucleotide polymorphisms.

In one embodiment the isolated polypeptide of this invention is a fragment of the native protein. In one embodiment, "fragment" refers to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment of this invention is an intrasequential section of the protein, peptide, or nucleic acid. In another embodiment, the fragment is a functional intrasequential section of the protein, peptide or nucleic acid. In another embodiment, the fragment is a functional intrasequential section within the protein, peptide or nucleic acid. In another embodiment, the fragment is an N-terminal functional fragment. In one embodiment, the fragment is a C-terminal functional fragment.

In one embodiment, the term "functional fragment" refers to a fragment that maintains a certain degree of biological activity as compared to the wild type despite it being a modified version of the native or wild type antibody or polypeptide. This degree of activity could range from moderate to high as compared to the wild type, where the "activity" refers to its natural biophysical or biochemical characteristics, e.g. binding ability, affinity, half-life, etc.

In one embodiment, an isolated polypeptide of this invention comprises a derivate of a polypeptide of this invention. "Derivative" is to be understood as referring, in some embodiments, to less than the full-length portion of the native sequence of the protein in question. In some embodiments, a "derivative" may further comprise (at its termini and/or within said sequence itself) non-native sequences, i.e. sequences which do not form part of the native protein in question. The term "derivative" also includes within its scope molecular species produced by conjugating chemical groups to the amino residue side chains of the native proteins or fragments thereof, wherein said chemical groups do not form part of the naturally-occurring amino acid residues present in said native proteins.

In one embodiment, the invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

In another embodiment, the polynucleotides are obtained, and the nucleotide sequence of the polynucleotides determined, by any method known in the art. Alternatively, a polynucleotide encoding an antibody (including molecules comprising, or alternatively consisting of, antibody fragments or variants thereof) are generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g. a cDNA clone from a cDNA library that encodes the antibody Amplified nucleic acids generated by PCR may then be cloned into replicable cloning vectors using any method well known in the art Methods of making antibodies and antibody fragments are known in the art. (See for example, Harlow and Lane, Antibodies: A Laboratory Manual, Cold Spring Harbor Laboratory, New York, 1988, incorporated herein by reference).

Antibodies can be produced by the immunization of various animals, including mice, rats, rabbits, goats, primates, humans and chickens with a target antigen such as TEM1 or peptide fragments of TEM1 containing the anti-TEM1 epitope of the present invention. In one embodiment, the antibody or antigen-binding fragment is purified prior to immunization of the animal. In one embodiment, the antibody or antigen-binding fragment of the present invention can be purified by methods known in the art, for example, gel filtration, ion exchange, affinity chromatography, etc. Affinity chromatography or any of a number of other techniques known in the art can be used to isolate polyclonal or monoclonal antibodies from serum, ascites fluid, or hybridoma supernatants.

"Purified" means that the monoclonal antibody is separated from at least some of the proteins normally associated with the monoclonal antibody and preferably separated from all cellular materials other than proteins.

In some embodiments, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding a protein or peptide, or fragments thereof, retaining wild type function exhibiting the same biological effect, despite these variations. Each of these represents a separate embodiment of the present invention.

The nucleic acids of the present invention can be produced by any synthetic or recombinant process such as is well known in the art. Nucleic acids according to the invention can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. The invention further provides DNA sequences which encode proteins similar to those encoded by sequences as described herein, but which differ in terms of their codon sequence due to the degeneracy of the genetic code or allelic variations (naturally-occurring base changes in the species population which may or may not result in an amino acid change), which may encode the proteins of the invention described herein, as well. Variations in the DNA sequences, which are caused by point mutations or by induced modifications (including insertion, deletion, and substitution) to enhance the activity, half-life or production of the polypeptides encoded thereby, are also encompassed in the invention.

DNA encoding the antibodies or antigen-binding fragments provided herein is readily isolated and sequenced using conventional procedures (e.g., by using oligonucleotide probes that are capable of binding specifically to genes encoding the heavy and light chains of the antibodies). Hybridoma cells serve as a source of such DNA. Once isolated, the DNA may be placed into expression vectors, which are then transfected into host cells such as E. coli cells, simian COS cells, Chinese hamster ovary (CHO) cells, yeast cells or myeloma cells that do not otherwise produce immunoglobulin protein, to obtain the synthesis of the antibodies in the recombinant host cells. Recombinant production of antibodies is described in more detail below.

It is to be understood by a skilled artisan that the antibody, antigen-binding fragments, or compositions provided herein can be used in therapeutic or diagnostic procedures.

In one embodiment, provided herein is a method of treating a tumor in a subject, whereby the method comprises the step of contacting said tumor cell with a therapeutically effective amount of an antibody or antigen-binding fragment provided herein that is operably linked to a biologically active agent.

In one embodiment, the term "operably linked" refers to the positioning/linking of the two or more molecules or sequences in such a manner as to ensure the proper function or expression of the molecule and sequence.

In one embodiment, the term "therapeutically effective amount" refers to an amount that provides a therapeutic effect for a given condition and administration regimen. In the present invention, the therapeutic effect is an increase in erythrocyte levels, which can be evidenced by a rise in hematocrit in the patient being treated.

In one embodiment, the term "preventing, or treating" refers to any one or more of the following: delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics. In one embodiment, "treating" refers to both therapeutic treatment and prophylactic or preventive measures, wherein the object is to prevent or lessen the targeted pathologic condition or disorder as described hereinabove.

In another embodiment, "symptoms" are manifestation of a disease or pathological condition as described hereinabove.

In another embodiment, the methods provided herein further comprise proteolytic inhibitors, pharmaceutical carriers, diluents, and adjuvants.

In another embodiment, provided herein is a method of treating angiogenesis of a solid tumor in a subject. In another embodiment, the method comprises the step of contacting a pericyte of the solid tumor with the antibody or antigen-binding fragment provided herein wherein the antibody or antigen-binding fragment is operably linked to a biologically active agent provided herein.

In another embodiment, provided herein is a method of treating angiogenesis of a solid tumor in a subject. In another embodiment, the method comprises the step of contacting a pericyte of the solid tumor with a pharmaceutical composition comprising the antibody or antigen-binding fragment provided herein operably linked to a biologically active agent provided herein.

In one embodiment the compositions of this invention comprise a polypeptide, antibody, or antigen-binding fragment of this invention, alone or in some embodiments, in combination with a second pharmaceutically active agent. In one embodiment, the term "pharmaceutically active agent" refers to any medicament which satisfies the indicated purpose. In some embodiments, the pharmaceutically active agent of this invention includes, but is not limited to a decongestant, antibiotic, bronchodilator, anti-inflammatory steroid, leukotriene antagonist or histamine receptor antagonist, and the like.

In another embodiment, provided herein is a method of delivering a biologically active agent and the antibody or antigen-binding fragment of the present invention for the treatment of a tumor in a subject. In another embodiment, the method comprises the step of concomitantly but individually administering the biologically active agent and the antibody or antigen-binding fragment. In another embodiment, the method comprises the step of separately administering the biologically active agent and the antibody or antigen-binding fragment.

In one embodiment, the antibody or antigen-binding fragment provided herein are themselves "biologically active", meaning they are able to exert the biological action or an enhanced action of their corresponding parental antibodies even after modification, in particular in binding to the target antigen, inhibiting binding of ligands to receptors, further in terms of modulation, in particular inhibition of antigen-mediated signal transduction and prophylaxis or therapy of antigen-mediated diseases. The term "biologically active", when used in reference to any of the biologically active agents described herein also refers to the agent's ability to modulate the immune response in a manner that can lead to a preventive, diagnostic, or therapeutic effect as will be understood by a skilled artisan. In some embodiments, agents that are used to achieve this biological activity include but are not limited to a cytokine, an enzyme, a chemokine, a radioisotope, an enzymatically active toxin, a therapeutic nano particle or a chemotherapeutic agent, as will be understood by a skilled artisan.

In an alternate embodiment, the polypeptides of antibodies are conjugated or operably linked so as to function in their intended purpose to an enzyme in order to employ Antibody Dependent Enzyme Mediated Prodrug Therapy (ADEPT). ADEPT may be used by conjugating or operably linking the antibody or Fc fusion to a prodrug-activating enzyme that converts a prodrug (e.g. a peptidyl chemotherapeutic agent) to an active anti-cancer drug. The enzyme component of the immunoconjugate useful for ADEPT includes any enzyme capable of acting on a prodrug in such a way so as to convert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; β-lactamase useful for converting drugs derivatized with a-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, Nature 328: 457-458). Polypeptide/antibody-abzyme conjugates can be prepared for delivery of the abzyme to a tumor cell population. Other additional modifications of the modified molecules provided herein are contemplated herein. For example, the polypeptide/antibody may be linked to one of a variety of nonproteinaceous polymers, e.g., polyethylene glycol (PEG), polypropylene glycol, polyoxyalkylenes, or copolymers of polyethylene glycol and polypropylene glycol.

In another embodiment, the antibody/polypeptide provided herein is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but are not limited to: non-steroidal anti-inflammatory drugs (NSAIDs) such as aspirin, ibuprofen, celecoxib, diclofenac, etodolac, fenoprofen, indomethacin, ketorolac, oxaprozin, nabumentone, sulindac, tolmentin, rofecoxib, naproxen, ketoprofen, and nabumetone; steroids (e.g. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFN-α IFN-β, IFN-γ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGF-β, TNF-α, TNF-β, TNF-R1, T-cell receptor, including Enbrel®. (etanercept), Humira®. (adalimumab), and Remicade®. (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (e.g. leflunomide), methotrexate, minocycline, mizoribine, mycophenolate mofetil, rapamycin, and sulfasasazine.

In an alternate embodiment, antibodies of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

A chemotherapeutic or other cytotoxic agent may be administered as a prodrug. The term "prodrug" refers to a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies/polypeptides of the compositions and methods provided herein include but are not limited to any of the aforementioned chemotherapeutic agents.

In some embodiments, any combination of the antibody/polypeptide with the biological active agents specified above, i.e., a cytokine, an enzyme, a chemokine, a radioisotope, an enzymatically active toxin, or a chemotherapeutic agent can be applied. In another embodiment, the antibody/polypeptide can be operably-linked with the biologically active agent and used in the methods described herein or antibody/polypeptide provided herein can merely be used in combination with the biologically active agents, in a manner in which both are administered separately (i.e.—not conjugated) to achieve the desired preventive, diagnostic, or therapeutic effect.

In one embodiment, provided herein is a method of inhibiting or suppressing a tumor in a subject. In another embodiment, the method comprises the step of administering an effective amount of the antibody or antigen-binding fragment of the present invention.

In another embodiment, provided herein is a method of delaying progression of a solid tumor in a subject. In yet another embodiment, the method comprises administering to the subject an effective amount of the antibody or antigen-binding fragment thereof provided herein. In another embodiment, the subject mounts an immune response against a pericyte of a vasculature of the solid tumor, thereby delaying progression of the solid tumor in the subject.

In one embodiment, provided herein is a method of diagnosing the presence of a tumor or a cancer growth in a subject. In another embodiment, the method comprises sampling a tissue sample isolated from the subject with a composition comprising the antibody or antigen-binding fragment provided herein, whereby specific binding of said antibody or antigen-binding fragment to the tissue sample is indicative of the presence of a tumor or cancer growth in the subject. In another embodiment, the method further comprises detecting a secondary reagent that specifically binds to the antibody or antigen-binding fragment but does not antagonize binding of the antibody or antigen-binding fragment to its target. In another embodiment, the "secondary reagent" is a photoactivatable agent, a fluorophore, a radioisotope, a bioluminescent protein, a bioluminescent peptide, a fluorescent tag, a fluorescent protein, or a fluorescent peptide.

In one embodiment, the term "cancer" and "cancerous" refer to or describe, in one embodiment, the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

In one embodiment, the term "cancer" includes but is not limited to, ovarian cancers, breast cancers, glioblastoma, gastrointestinal cancers. In another embodiment, the cancer is orthotopic ovarian cancer. In another embodiment, the ovarian cancer cell line MOV1 is used as a model of ovarian cancer in the present invention. It is to be understood by a skilled artisan that the invention is not limited to this cell line but includes other model cells lines available in the art.

In another embodiment, "sampling" comprises the step of testing or analyzing the sample using a detection assay that enables the detection of a secondary reagent that is complexed with or conjugated to the antibody or antigen-binding fragment and emits a detectable "signal" when the antibody or antigen-binding fragment is specifically bound to the target. In another embodiment, the detection is achieved using assays routinely used in the art such as, but not limited to immunological assays (for e g, immunohistochemistry, ELISA, etc.) or microscopic imaging.

In one embodiment, the term "labeled" refers to antibodies of the invention having one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and calorimetric dyes, or molecules such as biotin that enable other labeling methods. In one embodiment, antibodies of the invention are labeled with biotin. In other related embodiments, biotinylated antibodies of the invention may be used, for example, as an imaging agent or as a means of identifying one or more ligand molecules. In another embodiment, the label can be a nanoparticle that can be detected or visualized once bound to the antibody or antigen-binding fragment. Labels may be incorporated into the compound at any position and may be incorporated in vitro or in vivo during protein expression.

In one embodiment, the conjugate formed by the antibody or antigen-binding fragment and the secondary reagent provided herein are used for various applications such as, but not limited to, flow cytometry, ELISA, Western blotting, immunohistochemistry, membrane assays, and diagnostic and therapeutic methods as further described herein or as routinely applied in the art.

In one embodiment, an antibody of the present invention is administered to a patient having a disease involving inappropriate expression of a target antigen, a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the antibodies of the present invention.

In one embodiment, provided herein is a method of imaging a TEM1-containing tumor. In another embodiment, the method comprises the step of applying the antibody or to antigen-binding fragment provided herein that is operably linked to a secondary reagent. In another embodiment, the secondary reagent can be visualized once the antibody or antigen-binding fragment has bound its target. In yet another embodiment, the secondary reagent is a photoactivatable agent, a fluorophore, a radioisotope, a bioluminescent protein, a bioluminescent peptide, a fluorescent tag, a fluorescent protein, or a fluorescent peptide. Non-limiting examples of secondary reagents are provided below.

In one embodiment, the detectable label or secondary reagent attached thereto, include labels such as, but not limited to a fluorescent label (e.g., fluorescein, isothiocyanate (FITC), a cyanine dye, etc.), an affinity label (e.g., biotin, avidin, protein A, etc.), an enzymatic label (e.g., horseradish peroxidase or alkaline phosphatase), or an isotopic label (e.g., $^{125}$I) or any other such detectable moiety to allow for detection and isolation of the antibody.

Detection methods for identification of binding species within the population of altered variable regions can be direct or indirect and can include, for example, the measurement of light emission, radioisotopes, calorimetric dyes and fluorochromes. Direct detection includes methods that operate without intermediates or secondary measuring procedures to assess the amount of bound antigen or ligand. Such methods generally employ ligands that are themselves labeled by, for example, radioactive, light emitting or fluorescent moieties. In contrast, indirect detection includes methods that operate through an intermediate or secondary measuring procedure. These methods generally employ molecules that specifically react with the antigen or ligand and can themselves be directly labeled or detected by a secondary reagent. For example, a antibody specific for a ligand can be detected using a secondary antibody capable of interacting with the first antibody specific for the ligand, again using the detection methods described above for direct detection. Indirect methods can additionally employ detection by enzymatic labels. Moreover, for the specific example of screening for catalytic antibodies, the disappearance of a substrate or the appearance of a product can be used as an indirect measure of binding affinity or catalytic activity.

In specific embodiments, antibodies of the invention are labeled with Europium. For example, antibodies of the invention may be labelled with Europium using the DELFIA Eu-labeling kit (catalog #1244-302, Perkin Elmer Life Sciences, Boston, Mass.) following to manufacturer's instructions.

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N",N'''-tetraacetic acid (DOTA). In specific embodiments, the macrocyclic chelator is .quadrature.-(5-isothiocyanato-2-methoxyphenyl)-1,4,7,10-tetraaza-cyclodo-decane-1,4,7,10-tetraacetic acid. In other specific embodiments, the DOTA is attached to the antibody of the invention via a linker molecule. Examples of linker molecules useful for conjugating a macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2560, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

In one embodiment, provided herein is a method of biotinylating the antibodies or antigen-binding fragments provided herein. In another embodiment, the method comprises the step of mating the antibody-secreting yeast with a biotin ligase-bearing yeast. It is to be understood by a skilled artisan that other modifications some of which are provided herein and others which are routinely carried out in the art are encompassed within the invention.

In another embodiment, provided herein is a method of optimizing transformation and construct expression efficiency of a yeast strain. In another embodiment the method comprises the step of resuspending the yeast at room temperature, washing the yeast with water and lithium acetate at 4° C., incubating the yeast with the transforming vector without dimethyl sulfoxide (DMSO), heat shocking the yeast at 42° C. for 30 min, and allowing the yeast to recover in Yeast Peptone Dextrose (YPD) media for 2 hr.

In one embodiment, provided herein is a method of optimizing transformation and construct expression efficiency of a yeast strain. In another embodiment, the method comprises the step of preparing the construct under in the presence of 25 mM dithiothreitol (DTT), 20 mM Hepes, 0.6M sorbitol, followed by shaking for 30 min at 30° C.; and, transforming the yeast strain with the construct.

In one embodiment provided herein is a method of screening for and identifying an antibody or antigen-binding fragment thereof with optimized affinity for a tumor target/marker. In another embodiment, the method comprises displaying the antibody or antigen-binding fragment thereof on the surface of a yeast cell, testing its binding affinity to a marker or a pool of makers, and identifying the antibody or antigen-binding fragment that binds with the highest affinity to a desired marker.

In another embodiment, the "marker" is human or murine TEM1. In another embodiment, the antibody or antigen-binding fragment selectively binds with a high affinity to its target. In another embodiment, the range of the high affinity binding is between 0.05 to 0.1, nM. In another embodiment, the range of high affinity is between 0.1 to 0.5, nM. In another embodiment, the range of high affinity is between 0.5 to 1.0, nM.

In another embodiment, for the purposes of the invention, the terms "tumor marker", "tumor target", "target", "antigen" are all synonymous and refer to the compound/molecule that is specifically and selectively recognized by the antibody or antigen-binding fragment of the present invention.

In one embodiment, provided herein is a method of screening for an antibody or antigen-binding fragment thereof with optimized affinity for a tumor marker. In another embodiment, the method comprises transforming a yeast with a nucleic acid sequence encoding the antibody or antigen-binding fragment in secretable form, testing the binding affinity of the secreted antibody or antigen-binding fragment thereof to a marker or pool of markers, and identifying an antibody or antigen-binding fragment that binds with the highest affinity to the marker. Methods for screening for an antibodies that specifically bind to a target are provided for herein below.

In another embodiment, the term "transformed" refers to a genetic change in a cell following incorporation of nucleic acid (e.g., a transgene) exogenous to the cell. Thus, a "transformed cell" is a cell into which, or a progeny of which a nucleic acid molecule has been introduced by means of recombinant DNA techniques. Cell transformation to produce host cells may be carried out as described herein or using techniques known in the art. Accordingly, methods of producing cells containing the nucleic acids and cells expressing the antibodies or antigen-binding fragments of the invention are also provided.

In some embodiments, the present invention provides a library of antibodies or antigen-binding fragments for use in the methods and compositions of the present invention. Previously reported yeast libraries have been severely limited in size, with a maximum of $5 \times 10^6$, but typically less than $1 \times 10^5$, transformants per microgram of DNA for commonly used strains, resulting in insufficient diversity and potential for yielding high affinity antibodies. In one embodiment, provided herein is a display library of affinity-optimized antibodies or antigen-binding fragments of the present invention. In another embodiment, the library comprises up to $1 \times 10^8$ transformants per microgram of DNA. In another embodiment, the library is a yeast display library of affinity-optimized antibodies or antigen-binding fragments thereof.

In some embodiments, the library provided herein is a nucleic acid library, a phage display library, a yeast display library or an oligopeptide library. In some embodiments, the process yields a Fab fragment library, a FR library, a VH library, a VL library, a VH and VL library, a CDR library, or an ScFv yeast display library. According to this aspect of the invention, and in some embodiments, the invention provides a library of affinity-optimized antibodies or antigen-binding fragments thereof of known specificity prepared according to a process of the invention.

In another embodiment the library is a yeast library comprising a secretable form of an antibody or antigen-binding fragment of the present invention. In another embodiment, the library is derived from a thrombotic thrombocytopenic purpura (TTP) patient.

In one embodiment, the term "library" refers to a set antibodies or antigen-binding fragments, as described herein, in any form, including but not limited to a list of nucleic acid or amino acid sequences, a list of nucleic acid or amino acid substitutions at variable positions, a physical library comprising nucleic acids that encode the library sequences, or a physical library comprising the antibodies or antigen-binding fragments, either in purified or unpurified form. In another embodiment, the term refers to a set of antibodies or antigen-binding fragments displayed in any form as indicated above, but on the surface of a yeast cell. Accordingly, there are a variety of techniques that may be used to efficiently generate libraries of the present invention. Such methods that may find use in the present invention are described or referenced in U.S. Pat. No. 6,403,312; U.S. Ser. No. 09/782,004; U.S. Ser. No. 09/927,790; U.S. Ser. No. 10/218,102; PCT WO 01/40091; and PCT WO 02/25588, all incorporated entirely by reference. Such methods include but are not limited to gene assembly methods, PCR-based methods and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode the antibodies or antigen-binding fragments display libraries provided herein.

Recombinant antibody libraries can be expressed on the surface of yeast cells, phages or bacterial cells. Methods for preparing and screening libraries expressed on the surface of yeast cells are described further in International Application Publication No. WO 99/36569. Methods for preparing and screening libraries expressed on the surface of bacterial cells are described further in U.S. Pat. No. 6,699,658.

In one embodiment, a "yeast display library" refers to a collection of yeast (for e.g., *Saccharomyces cerevisiae*, *Saccharomyces pombe*) wherein the yeast express an external (typically heterologous) protein, (e.g. an scFv). The external protein is free to interact with (bind to) other moieties with which the yeast cells are contacted. Each yeast displaying an external protein is a "member" of the yeast display library.

In some embodiments, yeast-display offers several advantages over prokaryotic systems, including superior sampling of the immune antibody repertoire; post-translational modifications (glycosylation) due to the eukaryotic expression; fastar and more controlled flow cytrometry-based selection compared to solid phase panning; and absence of growth bias, as recombinant proteins are displayed at the yeast cell surface only during the induction step in the presence of galactose.

In one embodiment, a "phage display library" refers to a collection of phage (e.g., filamentous phage) wherein the phage expresses an external (typically heterologous) protein. The external protein is free to interact with (bind to) other moieties with which the phage are contacted. Each phage displaying an external protein is a "member" of the phage display library.

The term "filamentous phage" or "filamentous bacteriophage" refers to a viral particle capable of displaying a heterogenous polypeptide on its surface. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. The filamentous phage may contain a selectable marker such as tetracycline (e.g., "fd-tet"). Various filamentous phage display systems are well known to those of skill in the art (see, e.g., Zacher et al. (1980) Gene 9: 127-140, Smith et al. (1985) Science 228: 1315-1317 (1985); and Parmley and Smith (1988) Gene 73: 305-318).

An assembly cell is a cell in which a nucleic acid can be packaged into a viral coat protein (capsid). Assembly cells may be infected with one or more different virus particles (e.g. a normal or debilitated phage and a helper phage) that individually or in combination direct packaging of a nucleic acid into a viral capsid.

In one embodiment, phage display is used to create the ScFv variant library. In another embodiment, the method of preparing a phage display library comprises in some embodiments, the steps of modifying a phagemid vector for cloning, assembling VH and VL variable FR regions, followed by sequencing analysis, sequential cloning of VL and VH into the phagemid vector, and building a large size library. In another embodiment, the library of VH and VL gene segments from yeast display scFv libraries are constructed consist of both the Framework resides (FR1-1-R4) interspersed with CDRs 1-3.

Introduction of nucleic acid encoding an antibody or antigen-binding fragment into target cells can also be carried out by conventional methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes.

The use of liposomes for introducing various compositions into cells, including nucleic acids, is known to those skilled in the art (see, e.g., U.S. Pat. Nos. 4,844,904, 5,000,959, 4,863,740, and 4,975,282). A carrier comprising a natural polymer, or a derivative or a hydrolysate of a natural polymer, described in WO 94/20078 and U.S. Pat. No. 6,096,291, is suitable for mucosal delivery of molecules, such as polypeptides and polynucleotides. Piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, viral and non-viral vector means of delivery into cells or tissue, in vitro, in vivo and ex vivo are included.

In one embodiment, nucleotide sequences can be "operably linked", i.e., positioned, to ensure the functioning of an expression control sequence. These expression constructs are typically replicable in the cells either as episomes or as integral parts of the cell's chromosomal DNA, and may contain appropriate origins of replication for the respective prokaryotic strain employed for expression. Commonly, expression constructs contain selection markers, such as for example, tetracycline resistance, ampicillin resistance, kanamycin resistance or chlormaphenicol resistance, facilitating detection and/or selection of those bacterial cells transformed with the desired nucleic acid sequences (see, e.g., U.S. Pat. No. 4,704,362). These markers, however, are not exclusionary, and numerous others may be employed, as known to those skilled in the art. In another embodiment of the present invention expression constructs contain both positive and negative selection markers.

Similarly reporter genes may be incorporated within expression constructs to facilitate identification of transcribed products. Accordingly, in one embodiment of the present invention, reporter genes utilized are selected from the group consisting of β-galactosidase, chloramphenicol acetyl transferase, luciferase and a fluorescent protein.

Prokaryotic promoter sequences regulate expression of the encoded polynucleotide sequences, and in some embodiments of the present invention, are operably linked to polynucleotides encoding the polypeptides of this invention. In additional embodiments of the present invention, these promoters are either constitutive or inducible, and provide a means of high and low levels of expression of the polypeptides of this invention, and in some embodiments, for regulated expression of multiple polypeptides of the invention, which in some embodiments are expressed as a fusion protein.

Many well-known bacterial promoters, including the T7 promoter system, the lactose promoter system, typtophan (Trp) promoter system, Trc/Tac Promoter Systems, beta-lactamase promoter system, tetA Promoter systems, arabinose regulated promoter system, Phage T5 Promoter, or a promoter system from phage lambda, may be employed, and others, as well, and comprise embodiments of the present invention. The promoters will typically control expression, optionally with an operator sequence and may include ribosome binding site sequences for example, for initiating and completing transcription and translation. According to additional embodiments, the vector may also contain expression control sequences, enhancers that may regulate the transcriptional activity of the promoter, appropriate restriction sites to facilitate cloning of inserts adjacent to the promoter and other necessary information processing sites, such as RNA splice sites, polyadenylation sites and transcription termination sequences as well as any other sequence which may facilitate the expression of the inserted nucleic acid.

In another embodiment, the present invention comprises methods of use of a polynucleotide, vector, polypeptide and/or fragment thereof as herein described and/or compositions comprising the same in treating, inhibiting or preventing.

In another embodiment, the present invention comprises methods of use of a polynucleotide, vector, antibodies and/or fragment thereof as herein described and/or compositions comprising the same in treating, inhibiting or preventing.

Sequence alignment methods that can be used to achieve the desired sequence alignment include in some embodiments, but are not solely restricted to pair-wise alignment methods or multiple-sequence alignment methods, as will be understood by a skilled artisan. Sequence alignments can be stored in a wide variety of text-based file formats. In one embodiment, this is achieved by converting in certain embodiments, any format, for example a FASTA or Gen-Bank, SwissProt, Entrez and EMBL format, using conversion programs and programming packages such as, READ-SEQ, EMBOSS and BioPerl, BioRuby. It is to be understood that a skilled artisan can convert, modify, score, update and/or store the sequences as necessary using any program or storage media, as will be appreciated by the skilled artisan.

In some embodiments, the term "sequence alignment" includes use of any program or method, as understood by a skilled artisan, that is used to perform nucleic acid or amino acid sequence alignments to yield results that can be readily probed, assessed and subjected to mathematical and statistical calculations. In one embodiment, methods for sequence or structure alignment are well known in the art, and include alignments based on sequence and structural homology, as will be understood by a skilled artisan.

In one embodiment, the term "homology," "homolog" or "homologous" refer to sequence identity, or to structural identity, or functional identity. By using the term "homology" and the other like forms, it is to be understood that any molecule, whether nucleic acid or peptide, that functions similarly, and/or contains sequence identity, and/or is conserved structurally so that it approximates the reference sequence, is to be considered as part of this invention. In another embodiment, the terms "homology", "homologue" or "homologous", in any instance, indicate that the sequence referred to, whether an amino acid sequence, or a nucleic acid sequence, exhibits at least 86% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% or more correspondence with the indicated sequence. In another embodiment, the amino acid sequence or nucleic acid sequence exhibits 97%-100% correspondence to the indicated sequence. In another embodiment, the amino acid sequence or nucleic acid sequence exhibits 100% correspondence to the indicated sequence. Similarly, in one embodiment, the reference to a correspondence to a particular sequence includes both direct correspondence, as well as homology to that sequence as herein defined. Accordingly and in one embodiment, the term "non-homologous" refers the amino acid sequence or nucleic acid sequence exhibits no more than 85% correspondence with the indicated sequence. In another embodiment, the amino acid sequence or nucleic acid sequence exhibits no more than 75% correspondence with the indicated sequence. In another embodiment, the amino acid sequence or nucleic acid sequence exhibits no more than 65-74% correspondence with the indicated sequence. In another embodiment, the amino acid sequence or nucleic acid sequence exhibits no more than 55-64% correspondence with the indicated sequence. In another embodiment, the amino acid sequence or nucleic acid sequence exhibits no more than 45-54% correspondence with the indicated sequence. In another embodiment, the amino acid sequence or nucleic acid sequence exhibits no more than 35-44% correspondence with the indicated sequence. In another embodiment, the amino acid sequence or nucleic acid sequence exhibits no more than 35-44% correspondence with the indicated sequence. In another embodiment, the amino acid sequence or nucleic acid sequence exhibits no more than 15-34% correspondence with the indicated sequence. In another embodiment, the amino acid sequence or nucleic acid sequence exhibits no more than 5-14% correspondence with the indicated sequence. In another embodiment, the amino acid sequence or nucleic acid sequence exhibits no more than 0.1-4% correspondence with the indicated sequence. In another embodiment, the term "non-homologous can be used interchangeably with the term "low sequence similarity".

In one embodiment, the invention also provides transformed cells and progeny thereof into which a nucleic acid molecule encoding an antibody or antigen-binding fragment, has been introduced by means of recombinant DNA techniques in vitro, ex vivo or in vivo. The transformed cells can be propagated and the introduced nucleic acid transcribed, or encoded protein expressed. It is understood that a progeny cell may not be identical to the parental cell, since there may be mutations that occur during replication. Transformed cells include but are not limited to prokaryotic and eukaryotic cells such as bacteria, fungi, plant, insect, and animal (e.g., mammalian, including human) cells. The cells may be present in culture, in a cell, tissue or organ ex vivo or present in a subject.

Typically cell transformation employs a vector. The term "vector," refers to, e.g., a plasmid, virus, such as a viral vector, or other vehicle known in the art that can be manipulated by insertion or incorporation of a nucleic acid, for genetic manipulation (i.e., "cloning vectors"), or can be used to transcribe or translate the inserted polynucleotide (i.e., "expression vectors"). Such vectors are useful for introducing nucleic acids, including a nucleic acid that encodes a humanized antibody operably linked with an expression control element, and expressing the encoded protein in vitro (e.g., in solution or in solid phase), in cells or in vivo.

In one embodiment, the expression vector(s) is(are) transferred to a host cell by conventional techniques and the transfected cells are then cultured by conventional techniques to produce an antibody or antigen-binding fragment of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In other embodiments, for the expression of entire antibody molecules, vectors encoding both the heavy and light chains are co-expressed in the host cell for expression of the entire immunoglobulin molecule.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants thereof (single chain antibodies), microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (11990); Bebbington et al., Bio/Techniques 10:169 (1992); Keen and Hale, Cytotechnology 18:207 (1996)). These references are incorporated in their entireties by reference herein.

A vector used to transform a cell or a host-expression vector generally contains at least an origin of replication for propagation in the cell. Control elements, including expression control elements as set forth herein, present within a vector, are included to facilitate transcription and translation. The term "expression control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, etc.

Vectors can include a selection marker. As is known in the art, "selection marker" means a gene that allows for the selection of cells containing the gene. "Positive selection" refers to a process whereby only cells that contain the selection marker will survive upon exposure to the positive selection. Drug resistance is one example of a positive selection marker; cells containing the marker will survive in culture medium containing the selection drug, and cells which do not contain the marker will die. Such markers include drug resistance genes such as neo, which confers resistance to G418, hygr, which confers resistance to hygromycin, or puro which confers resistance to puromycin, among others. Other positive selection marker genes include genes that allow identification or screening of cells containing the marker. These genes include genes for fluorescent proteins (GFP), the lacZ gene, the alkaline phosphatase gene, and surface markers such as CD8, among others.

Vectors can contain negative selection markers. "Negative selection" refers to a process whereby cells containing a negative selection marker are killed upon exposure to an appropriate negative selection agent. For example, cells which contain the herpes simplex virus-thymidine kinase (HSV-tk) gene (Wigler et al., *Cell* 11:223 (1977)) are sensitive to the drug gancyclovir (GANC). Similarly, the gpt gene renders cells sensitive to 6-thioxanthine.

Mammalian expression systems further include vectors specifically designed for in vivo and ex vivo expression. Such systems include adeno-associated virus (AAV) vectors (U.S. Pat. No. 5,604,090). AAV vectors have previously been shown to provide expression of Factor IX in humans and in mice at levels sufficient for therapeutic benefit (Kay et al., *Nat. Genet.* 24:257 (2000); Nakai et al., *Blood* 91:4600 (1998)). Adenoviral vectors (U.S. Pat. Nos. 5,700,470, 5,731,172 and 5,928,944), herpes simplex virus vectors (U.S. Pat. No. 5,501,979) and retroviral (e.g., lentivirus vectors are useful for infecting dividing as well as non-dividing cells and foamy viruses) vectors (U.S. Pat. Nos. 5,624,820, 5,693,508, 5,665,577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed and also may be used (see, e.g., U.S. Pat. Nos. 5,821,235, 5,786,340 and 6,110,456). In yeast, vectors that facilitate integration of foreign nucleic acid sequences into a chromosome, via homologous recombination, for example, are known in the art and can be used. Yeast artificial chromosomes (YAC) are typically used when the inserted nucleic acids are too large for more conventional vectors (e.g., greater than about 12 kb).

In one embodiment, phagemid vectors for use in the invention include any available in the art suitable for the production of the antibodies/antibody templates/FR libraries of the present invention and include phagemid vectors pCB04, pIT1, pIT2, CANTAB 6, pComb 3 HS. Filamentous vectors and methods of phagemid construction are described in, for example, U.S. Pat. No. 6,054,312 and U.S. Pat. No. 6,803,230, each incorporated herein by reference. Bacteriophage display systems involving non-filamentous bacteriophage vectors known as cytoplasmic bacteriophage or lytic phage can also be utilized as described in for example, U.S. Pat. No. 5,766,905, incorporated herein by reference.

Suitable bacterial expression constructs for use with the present invention include, but are not limited to the pCAL, pUC, pET, pETBlue™ (Novagen), pBAD, pLEX, pTrcHis2, pSE280, pSE380, pSE420 (Invitrogen), pKK223-2 (Clontech), pTrc99A, pKK223-3, pRIT2T, pMC1871, pEZZ 18 (Pharmacia), pBluescript II SK (Stratagene), pALTER-Ex1, pALTER-Ex2, pGEMEX (Promega), pFivE (MBI), pQE (Qiagen) commercially available expression constructs, and their derivatives, and others known in the art. In some embodiments of the present invention the construct may also include, a virus, a plasmid, a bacmid, a phagemid, a cosmid, or a bacteriophage.

In one embodiment, provided herein is a vector encoding the display library of the present invention. In another embodiment, the vector is pAGA2.

In another embodiment, provided herein is a vector encoding the secretable library of the present invention. In another embodiment, the vector is p416BCCP.

Antibodies may be screened using a variety of methods, including but not limited to those that use in vitro assays, in vivo and cell-based assays, and selection technologies. Properties of antibodies that may be screened include but are not limited to stability, solubility, and affinity for the target. Multiple properties may be screened simultaneously or individually. Proteins may be purified or unpurified, depending on the requirements of the assay. In one embodiment, the screen is a qualitative or quantitative binding assay for binding of antibodies to a protein or nonprotein molecule that is known or thought to bind the antibody. In one embodiment, the screen is a binding assay for measuring binding to the target antigen. Automation and high-throughput screening technologies may be utilized in the screening procedures. Screening may employ the use of a fusion partner or label. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as Biacore™), isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

In some embodiments, the screening of populations of polypeptides such as the altered variable region populations produced by the methods of the invention, involve immobilization of the populations of altered variable regions to filters or other solid substrate. This is particularly advantageous because large numbers of different species can be efficiently screened for antigen binding. Such filter lifts will allow for the identification of altered variable regions that exhibit substantially the same or greater binding affinity compared to the donor variable region. Alternatively, if the populations of altered variable regions are expressed on the surface of a cell, a yeast or bacteriophage, for example, panning on immobilized antigen can be used to efficiently screen for the relative binding affinity of species within the population.

Another affinity method for screening populations of altered variable regions polypeptides is a capture lift assay that is useful for identifying a binding molecule having selective affinity for a ligand (Watkins et. al., (1997)). This method employs the selective immobilization of altered variable regions to a solid support and then screening of the selectively immobilized altered variable regions for selective binding interactions against the cognate antigen or binding partner. Selective immobilization functions to increase the sensitivity of the binding interaction being measured since initial immobilization of a population of altered variable regions onto a solid support reduces non-specific binding interactions with irrelevant molecules or contaminants which can be present in the reaction.

Another method for screening populations or for measuring the affinity of individual altered variable region polypeptides is through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates (kon) and disassociation rates (koff). Methods for measuring the affinity, including association and disassociation rates using surface plasmon resonance are well known in the arts and can be found described in, for example, Jonsson and Malmquist, Advances in Biosnsors, 2:291-336 (1992) and Wu et al. Proc. Natl. Acad. Sci. USA, 95:6037-6042 (1998). Moreover, one apparatus well known in the art for measuring binding interactions is a BIAcore 2000 instrument which is commercially available through Pharmacia Biosensor, (Uppsala, Sweden).

The pharmacokinetics (PK) of the antibodies of the invention can be studied in a variety of animal systems, with the most relevant being non-human primates such as the cynomolgus, rhesus monkeys. Single or repeated i.v./s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life ($T_{1/2}$). Additional measured parameters could include compartmental analysis of concentration-time data obtained following i.v. administration and bioavailability.

In another embodiment, toxicity studies are performed to determine the antibody effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The biophysical properties of antibodies, for example stability and solubility, may be screened using a variety of methods known in the art. Protein stability may be determined by measuring the thermodynamic equilibrium between folded and unfolded states. For example, antibodies of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use in the present invention for characterizing the biophysical properties of antibodies include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility is measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

The biological properties of the antibodies of the present invention may be further characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the antibodies of the present invention, a particular challenge arises when using animal models to evaluate the potential for in-human efficacy of candidate polypeptides—this is due, at least in part, to the fact that antibodies that have a specific effect on the affinity for a human Fc receptor may not have a similar affinity effect with the orthologous animal receptor. These problems can be further exacerbated by the inevitable ambiguities associated with correct assignment of true orthologs (Mechetina et al., Immunogenetics, 2002 54:463-468, incorporated entirely by reference), and the fact that some orthologs simply do not exist in the animal (e.g. humans possess an FcγRIIa whereas mice do not). Therapeutics are often tested in mice, including but not limited to nude mice, SCID mice, xenograft mice, and transgenic mice (including knockins and knockouts). For example, an antibody of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the antibody to reduce or inhibit cancer growth and metastasis. Such experimentation may provide meaningful data for determination of the potential of said antibody to be used as a therapeutic. Any organism, e.g., mammals, may be used for testing. For example because of their genetic similarity to humans, monkeys can be suitable therapeutic models, and thus may be used to test the efficacy, toxicity, pharmacokinetics, or other property of the antibodies of the present invention. Tests of the antibodies of the present invention in humans are ultimately required for approval as drugs, and thus of course these experiments are contemplated. Thus the antibodies of the present invention may be tested in humans to determine their therapeutic efficacy, toxicity, pharmacokinetics, and/or other clinical properties.

In one embodiment, the library provided herein is screened using one or more cell-based or in vitro assays. For such assays, antibodies, purified or unpurified, are typically added exogenously such that cells are exposed to individual variants or groups of variants belonging to a library. These assays are typically, but not always, based on the biology of the ability of the antibody to bind to antigen and mediate some biochemical event, for example effector functions like cellular lysis, phagocytosis, ligand/receptor binding inhibition, inhibition of growth and/or proliferation, apoptosis, etc. Such assays often involve monitoring the response of cells to antibody, for example cell survival, cell death, cellular phagocytosis, cell lysis, change in cellular morphology, or transcriptional activation such as cellular expression of a natural gene or reporter gene. For example, such assays may measure the ability of antibodies to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., humans, mice, rats, rabbits, monkeys, etc. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation, or activation to be monitored. In one embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an antibody. Cell types for such assays may be prokaryotic or eukaryotic, and a variety of cell lines that are known in the art may be employed. Alternatively, cell-based screens are performed using cells that have been transformed or transfected with nucleic acids encoding the antibodies. In one embodiment, example of such assays are provided herein, (see FIG. 8 and Example 5).

A variety of selection methods are known in the art that may find use in the present invention for screening protein libraries. These include but are not limited to yeast display, yeast-two-hybrid based screening. In other embodiments, further methods include phage display (Phage display of peptides and proteins: a laboratory manual, Kay et al., 1996, Academic Press, San Diego, Calif., 1996; Lowman et al., 1991, *Biochemistry* 30:10832-10838; Smith, 1985, *Science* 228:1315-1317) and its derivatives such as selective phage infection (Malmborg et al., 1997, *J Mol Biol* 273:544-551), selectively infective phage (Krebber et al., 1997, *J Mol Biol* 268:619-630), and delayed infectivity panning (Benhar et al., 2000, *J Mol Biol* 301:893-904), cell surface display (Witrrup, 2001, *Curr Opin Biotechnol*, 12:395-399) such as display on bacteria (Georgiou et al., 1997, *Nat Biotechnol* 15:29-34; Georgiou et al., 1993, *Trends Biotechnol* 11:6-10; Lee et al., 2000, *Nat Biotechnol* 18:645-648; June et al., 1998, *Nat Biotechnol* 16:576-80), yeast (Boder & Wittrup, 2000, *Methods Enzymol* 328:430-44; Boder & Wittrup, 1997, *Nat Biotechnol* 15:553-557), and mammalian cells (Whitehorn et al., 1995, *Bio/technology* 13:1215-1219), as well as in vitro display technologies (Amstutz et al., 2001, *Curr Opin Biotechnol* 12:400-405) such as polysome display (Mattheakis et al., 1994, *Proc Natl Acad Sci USA* 91:9022-9026), ribosome display (Hanes et al., 1997, *Proc Natl Acad Sci USA* 94:4937-4942), mRNA display (Roberts & Szostak, 1997, *Proc Natl Acad Sci USA* 94:12297-12302; Nemoto et al., 1997, *FEBS Lett* 414:405-408), and ribosome-inactivation display system (Zhou et al., 2002, *J Am Chem Soc* 124, 538-543).

Other selection methods that may find use in the present invention include methods that do not rely on display, such as in vivo methods including but not limited to periplasmic expression and cytometric screening (Chen et al., 2001, *Nat Biotechnol* 19:537-542), the protein fragment complementation assay (Johnsson & Varshavsky, 1994, *Proc Natl Acad Sci USA* 91:10340-10344; Pelletier et al., 1998, *Proc Natl Acad Sci USA* 95:12141-12146), and the yeast two hybrid screen (Fields & Song, 1989, *Nature* 340:245-246) used in selection mode (Visintin et al, 1999, *Proc Natl Acad Sci USA* 96:11723-11728). In an alternate embodiment, selection is enabled by a fusion partner that binds to a specific sequence on the expression vector, thus linking covalently or noncovalently the fusion partner and associated variant library member with the nucleic acid that encodes them. For example, U.S. Ser. No. 09/642,574; U.S. Ser. No. 10/080, 376; U.S. Ser. No. 09/792,630; U.S. Ser. No. 10/023,208; U.S. Ser. No. 09/792,626; U.S. Ser. No. 10/082,671; U.S. Ser. No. 09/953,351; U.S. Ser. No. 10/097,100; U.S. Ser. No. 60/366,658; PCT WO 00/22906; PCT WO 01/49058; PCT WO 02/04852; PCT WO 02/04853; PCT WO 02/08023; PCT WO 01/28702; and PCT WO 02/07466 describe such a fusion partner and technique that may find use in the present invention. In an alternative embodiment, in vivo selection can occur if expression of the protein imparts some growth, reproduction, or survival advantage to the cell.

Methods of identifying antibodies through their binding affinities or specificities are very well known in the art and include methods such as immunoprecipitation or an in vitro binding assay, such as radioimmunoassay (RIA) or enzyme-linked immunoabsorbent assay (ELISA). Other well-known methods can be used to determine antibody binding affinities and these methods can be readily used, as will be understood by a skilled artisan. In that regard, the method of the present invention further comprises determining a respective binding affinity for a target for each of said antibodies in said library formed. In another embodiment the method further comprises identifying an antibody having the highest binding affinity for said target. According to this aspect, and in one embodiment, this invention to provides a humanized antibody optimized for affinity to a known target identified by the methods of this invention. Antibodies with known specificity are prepared and their affinity assessed. Antibodies with known specificity whose affinity is desired to be optimized by the methods of this invention may be constructed by any means known in the art. For example, monoclonal antibodies may be produced in a number of ways, including using the hybridoma method (e.g. as described by Kohler et al., Nature, 256: 495, 1975, herein incorporated by reference), or by recombinant DNA methods (e.g., U.S. Pat. No. 4,816,567, herein incorporated by reference).

Once an antibody of interest has been identified from a library, DNAs encoding the light and heavy chains of the antibody can be isolated by standard molecular biology techniques, such as by polymerase chain reaction (PCR) amplification of DNA from the display package (e.g., phage, yeast) isolated during the library screening process. Nucleotide sequences of antibody light and heavy chain genes from which oligonucleotide primers can be prepared are known in the art. For example, many such sequences are disclosed in Kabat et al. (1991) supra and in the "Vbase" human germline sequence database, administered by the MRC Centre for Protein Engineering (Cambridge, UK) (website: http://www.mrc-cpe.cam.ac.uk/vbase-intro.php?menu=901).

The antibodies of the present invention may find use in a wide range of products. In one embodiment the antibody of the invention is a therapeutic, a diagnostic, or a research reagent. In one embodiment, an antibody of the invention is a therapeutic. In some embodiments, the antibody or antigen-binding fragment of the present invention is used for agricultural or industrial uses. An antibody of the present invention may find use in an antibody composition that is monoclonal or polyclonal. The antibodies of the present invention may be agonists, antagonists, neutralizing, inhibitory, or stimulatory. In one embodiment, the antibodies of the present invention are used to kill target cells that bear the target antigen, for example cancer cells. In an alternate embodiment, the antibodies of the present invention are used to block, antagonize, or agonize the target antigen. In an alternate embodiment, the antibodies of the present invention are used to block, antagonize, or agonize the target antigen and kill the target cells that bear the target antigen. In another embodiment, the target cell is a tumor cell or it's pericyte. In one embodiment, pericytes are play an important role in angiogenesis and are also considered to be a target of the antibodies or antigen-binding fragments provided herein.

The invention also provides a kit for preparing a library of human antibody templates. In this regard, the kit comprises a library of polynucleotides encoding human antibody templates comprising Framework Region (FR) regions possessing residues comprising a positive complementarity determining region (CDR) contact ratio score and a positive human diversity score or a positive B to M score and a positive human diversity score as described herein above.

The invention provides a kit for preparing a library of antibody or antigen-binding fragments thereof. In one embodiment, the kit comprises a vector comprising the polynucleotides encoding the antibody or antigen-binding fragments thereof of the invention, or in another embodiment, the kit comprises bacteriophages comprising the polynucleotides encoding the antibody or antigen-binding fragments thereof of the invention. In another embodiment, the kit comprises yeast expressing the antibody or antigen-binding fragments thereof of the invention The invention further provides kits comprising one or more compositions of the invention, including pharmaceutical formulations, packaged into suitable packaging material. In another embodiment, a kit includes a nucleic acid encoding the antibody or antigen-binding fragments thereof of the invention. In additional embodiments, a kit includes nucleic acids that further include an expression control element; an expression vector; a viral expression vector; an adeno-associated virus expression vector; an adenoviral expression vector; and a retroviral expression vector. In yet an additional embodiment, a kit includes a cell that the antibody or antigen-binding fragments thereof of the invention.

In additional embodiments, a kit includes a label or packaging insert including instructions for expressing a humanized antibody or a nucleic acid encoding the antibody or antigen-binding fragments thereof in cells in vitro, in vivo, or ex vivo. In yet additional embodiments, a kit includes a label or packaging insert including instructions for treating a subject (e.g., a subject having or at risk of having asthma) with the antibody or antigen-binding fragments thereof of the invention in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating the common cold. Kits of the invention therefore can additionally include instructions for using the kit components in a method of the invention.

Instructions can include instructions for practicing any of the methods of the invention described herein. Thus, invention pharmaceutical compositions can be included in a container, pack, or dispenser together with instructions for administration to a subject. Instructions may additionally include indications of a satisfactory clinical endpoint or any adverse symptoms that may occur, or additional information required by the Food and Drug Administration for use on a human subject.

In one embodiment, polypeptides of the present invention are administered as part of a vaccine. In some embodiments, the term vaccine is to be understood to encompass any immunomodulating composition, and such vaccines may comprise an adjuvant, an antigen, an immuno-modulatory compound, or a combination thereof, in addition to the polypeptides of this invention.

In some embodiments, the adjuvant may include, but is not limited to: (A) aluminium compounds (e.g. aluminium hydroxide, aluminium phosphate, aluminium hydroxyphosphate, oxyhydroxide, orthophosphate, sulphate, etc. [e.g. see chapters 8 & 9 of ref. 96]), or mixtures of different aluminium compounds, with the compounds taking any suitable form (e.g. gel, crystalline, amorphous, etc.), and with adsorption being preferred; (B) MF59 (5% Squalene, 0.5% Tween 80, and 0.5% Span 85, formulated into submicron particles using a microfluidizer); (C) liposomes; (D) ISCOMs, which may be devoid of additional detergent; (E) SAF, containing 10% Squalane, 0.4% Tween 80, 5% pluronic-block polymer L121, and thr-MDP, either micro fluidized into a submicron emulsion or vortexed to generate a larger particle size emulsion; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21, also known as Stimulon™; (H) chitosan; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc.; (K) monophosphoryl lipid A (MPL) or 3-O-deacylated MPL (3dMPL)]; (L) combinations of 3dMPL with, for example, QS21 and/or oil-in-water emulsions; (M) oligonucleotides comprising CpG motifs] i.e. containing at least one CG dinucleotide, with 5-methylcytosine optionally being used in place of cytosine; (N) a polyoxyethylene ether or a polyoxyethylene ester; (O) a polyoxyethylene sorbitan ester surfactant in combination with an octoxynol or a polyoxyethylene alkyl ether or ester surfactant in combination with at least one additional non-ionic surfactant such as an octoxynol; (P) an immuno-stimulatory oligonucleotide (e.g. a CpG oligonucleotide) and a saponin; (Q) an immuno-stimulant and a particle of metal salt; (R) a saponin and an oil-in-water emulsion; (S) a saponin (e.g. QS21)+3dMPL+IL12 (optionally+a sterol); (T) E. coli heat-labile enterotoxin ("LT"), or detoxified mutants thereof, such as the K63 or R72 mutants; (U) cholera toxin ("CT"), or diphtheria toxin ("DT") or detoxified mutants of either; (V) double-stranded RNA; (W) monophosphoryl lipid A mimics, such as aminoalkyl glucosaminide phosphate derivatives e.g. RC-529]; (X) polyphosphazene (PCPP); or (Y) a bioadhesive such as esterified hyaluronic acid microspheres or a mucoadhesive such as crosslinked derivatives of poly(acrylic acid), polyvinyl alcohol, polyvinyl pyrollidone, polysaccharides and carboxymethylcellulose.

In some embodiments, administration of the compounds of this invention is intended to reduce the severity of the pathologic condition. By the term "reduce the severity of the pathologic condition", it is to be understood that any reduction via the methods, compounds and compositions disclosed herein, is to be considered encompassed by the invention. Reduction in severity may, in one embodiment comprise enhancement of survival, or in another embodiment, halting disease progression, or in another embodiment, delay in disease progression.

In one embodiment, dosing is dependent on the cellular responsiveness to the administered molecules/compounds or compositions comprising same. In general, the doses utilized for the above described purposes will vary, but will be in an effective amount to exert the desired effect, as determined by a clinician of skill in the art. As used herein, the term "pharmaceutically effective amount" refers to an amount of a compound as described herein, which will produce the desired alleviation in symptoms or other desired phenotype in a patient.

In one embodiment of the invention, the concentrations of the compounds will depend on various factors, including the nature of the condition to be treated, the condition of the patient, the route of administration and the individual tolerability of the compositions.

In some embodiments, any of the compositions of this invention will comprise a compound, in any form or embodiment as described herein. In some embodiments, any of the compositions of this invention will consist of a compound, in any form or embodiment as described herein. In some embodiments, any of the compositions of this invention will consist essentially of a compound, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry.

In some embodiments, the compositions of this invention will consist essentially of a polypeptide/polynucleotide/vector as herein described. In some embodiments, the term "consisting essentially of" refers to a composition whose only active ingredient of a particular class of agents, is the indicated active ingredient, however, other compounds may be included which are involved directly in the therapeutic effect of the indicated active ingredient. In some embodiments, the term "consisting essentially of" refers to a composition whose only active ingredient of targeting a particular mechanism, or acting via a particular pathway, is the indicated active ingredient, however, other compounds may be included which are involved directly in the therapeutic effect of the indicated active ingredient, which for example have a mechanism of action related to but not directly to that of the indicated agent. In some embodiments, the term "consisting essentially of" refers to a composition whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It will be appreciated that the actual amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention are administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In one embodiment, the route of administration may be parenteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation (aerosol), nasal aspiration (spray), intranasal (drops), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, body weight, and response of the individual patient.

For intranasal administration or application by inhalation, solutions or suspensions of the compounds mixed and aerosolized or nebulized in the presence of the appropriate carrier suitable. Such an aerosol may comprise any agent described herein.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

Sustained or directed release compositions can be formulated, e.g., liposomes or those wherein the active compound is protected with differentially degradable coatings, e.g., by microencapsulation, multiple coatings, etc. Such compositions may be formulated for immediate or slow release. It is also possible to freeze-dry the new compounds and use the lyophilisates obtained, for example, for the preparation of products for injection.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In one embodiment, a composition of or used in the methods of this invention may be administered alone or within a composition. In another embodiment, compositions of this invention admixture with conventional excipients, i.e., pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

Pharmaceutical compositions include "pharmaceutically acceptable" and "physiologically acceptable" carriers, diluents or excipients. In one embodiment, the terms "pharmaceutically acceptable" and "physiologically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration. The terms include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary active compounds (e.g., preservatives, antibacterial, antiviral and antifungal agents) can also be incorporated into the compositions.

Pharmaceutical compositions of the present invention can include one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-a), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

The compositions (e.g., antibodies, and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Pharmaceutical compositions can be formulated to be compatible with a particular local or systemic route of administration. Thus, pharmaceutical compositions include carriers, diluents, or excipients suitable for administration by particular routes. Specific non-limiting examples of routes of administration for compositions of the invention are inhalation or intranasal delivery. Additional routes include parenteral, e.g., intravenous, intradermal, subcutaneous, oral, transdermal (topical), transmucosal, and rectal administration.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride can be included in the composition. Including an agent which delays absorption, for example, aluminum monostearate and gelatin can prolong absorption of injectable compositions.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients as above. In the case of sterile powders for the preparation of sterile injectable solutions, methods of preparation include, for example, vacuum drying and freeze-drying which yields a powder of the active ingredient plus any additional desired ingredient from a previously sterile-filtered solution thereof.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdernal administration, the active compounds are formulated into ointments, salves, gels, or creams as generally known in the art.

The present invention's antibodies, including subsequences and modified forms and nucleic acids encoding them, can be prepared with carriers that protect against rapid elimination from the body, such as a controlled release formulation or a time delay material such as glyceryl monostearate or glyceryl stearate. The compositions can also be delivered using implants and microencapsulated delivery systems to achieve local or systemic sustained delivery or controlled release.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Additional pharmaceutical formulations appropriate for the compositions for administration in the methods of the invention are known in the art (see, e.g., *Remington's Pharmaceutical Sciences* (1990) $18^{th}$ ed., Mack Publishing Co., Easton, Pa.; *The Merck Index* (1996) $12^{th}$ ed., Merck Publishing Group, Whitehouse, N.J.; and *Pharmaceutical Principles of Solid Dosage Forms*, Technonic Publishing Co., Inc., Lancaster, Pa., (1993)). The pharmaceutical formulations can be packaged in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the pharmaceutical carrier or excipient.

Although the pharmaceutical compositions provided herein are principally directed to pharmaceutical compositions which are suitable for administration to humans, it will be understood by the skilled artisan that such compositions are generally suitable for administration to animals of all sorts. Modification of pharmaceutical composition suitable for administration to humans in order to render the compositions suitable for administration to various animals is well understood, and the ordinarily skilled veterinary pharmacologist can design and perform such modification with little, if any, experimentation. Subjects to which administration of the pharmaceutical compositions of the invention is contemplated include, but are not limited to, humans and other primates, and other mammals.

It is to be understood that any amino acid sequence, whether obtained naturally or synthetically by any means, exhibiting sequence, structural or functional homology to the polypeptides described herein, are considered part of this invention.

In one embodiment, the term "about" means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

It is to be understood that reference to any publication, patent application or issued patent is to be considered as fully incorporated herein by reference in its entirety.

It is to be understood that any assay for measuring a particular activity which is modulated by the therapeutic compound may be employed, as a means of determining the efficacy of the compound, in one embodiment, optimal loading of the compound, in another embodiment, timing and dosage, in another embodiment, or a combination thereof.

The following examples are presented in order to more fully illustrate the preferred embodiments of the invention. They should in no way be construed, however, as limiting the broad scope of the invention.

EXAMPLES

Materials and Methods:
Development of Companion Vectors for Yeast-Display and Yeast-Secretion of N-Terminal Biotinylated scFv The pAGA2 vector for yeast-display (FIG. 1c) was derived from shuttle vector p414 GAL1 (24) (the kind gift of Martin Funk, IMT, Philipps-Univ. Marburg, Germany) The pAGA2 multiple cloning site (MCS) was engineered as follows: the first site Nhe1 was inserted after a FLAG tag and a $(G_4S)_3$ linker sequence. The second site EcoR1 was part of a stop codon that is removed when cDNA is inserted in frame in the cloning site. The third site Xho1 was inserted just 5' to the c-myc tag, out of frame with the FLAG tag, to insure that both tags could be expressed only in the presence of correctly inserted cDNA.

The pAGA2 full insert sequence is: 5'-agtgatgcagttact-tcgctgtttttcaatattnctgttattgcttcagttttagcacaggaactgacaac-tatatgcgagcaaatcccctcac caactttagaatcgacgccgtactctttgtcaac-gactactattttggccaacgggaaggcaatgcaaggagtttttgaatattacaaatc agtaacgtttgtcagtaattgcggttctcaccccctcaacaactagcaaaggcagc-cccataaacacacagtatgatttgattataaagat gacgataaaggtggtggag-gtggttctggtggtggaggttctggtggtggtggatctgctagctgaattcctc-gagggatccgaacaa aagcttatttctgaagaagacttgtaa-3' (SEQ ID NO: 1). The PCR product was generated from oligonucleotide templates and elongated by primers including recombination sequences for gap repair cloning: 5 'Display 5'-caaggagaaaaaactatatctagaactagtgatgcagttacttcgctgatttc-3' (SEQ ID NO: 2) and 3'Display 5'-gtaagcgtgacataactaattacat-gactcgattacaagtcttcttcagaaataagcttttgttc-3) (SEQ ID NO: 3).

To construct the p416 BCCP vector, the companion vector of pAGA2 for the secretion of N-terminal biotinylated scFv (FIG. 1d), the shuttle vector p416 GAL1 (24) (the kind gift of Martin Funk) was linearized by BamH1 and Xho1, and co-transformed in yeast with a PCR product encoding alpha preproleader and RK endopeptidase sequences fused to a biotin accepting site (BCCP), IgA hinge, FLAG tag, $(G_4S)_3$ linker, cloning site with a stop codon, and V5-HIS tags.

The p416 BCCP full insert sequence is: 5'-atgagatttcct-tcaantttactgcagttttattcgcagcatcctccgcattagctgctccagtcaacac-tacaacaggagatgaaacggc acaaattccggctgaagctgtcatcggttactca-gatttagaaggggatttcgatgttgctgttttgccattttccaacagcacaaataacg ggttattgtttataaatactactattgccagcattgctgctaaagaagaagggg-tatctttggataaaagatgtgatggtttgaatgatattttt gaagctcaaaaaatt-gaatggcatgaaccatcaacaccaccaactccaagtccttctactcctcctacacct-tcaccatcagattataaa gatgacgataaaggtggtggaggtggttctggtggtggaggttctggtggtggtg-gatctgaattcgctagctaagtcgacggtaagc ctatccctaaccctctcctcg-gtctcgattctacgcatcatcaccatcaccat-3' (SEQ ID NO: 4).

Generation of rhTEM1-GST and rGST Recombinant Proteins and of TEM1-Transduced Cell Lines.

hTEM1 cDNA (NM_020404) was a kind gift from Dr. Ballmer-Hofer (Paul Scherrer Institut, Switzerland). The 1113 bp fragment corresponding to nucleotides 75-1187 of NM_020404 was cloned into the BamH1 site of the Glutathione S-transferase Gene Fusion Vector pGEX-2TK (Life Science, Piscataway, N.J.) to obtain hTEM1-pGEX-2TK plasmid. hTEM1-pGEX-2TK and the control vector pGEX-2TK were transformed into E. coli BL21-CodonPlus(DE3)-RIPL (Stratagene, Cedar Creek, Tex.) to produce human TEM1 recombinant protein fused to GST (rhTEM1-GST) and GST recombinant protein (rGST). Transformants were inoculated into fresh 2YT medium and incubated at 37° C. on an orbital shaker (200 rpm) overnight. Each sample was then inoculated into 500 mL of fresh medium at a dilution of 1:50, and incubated in a shaking incubator at 37° C. until the OD600 was 0.8. Isopropyl β-d-1-thiogalactopyranoside (IPTG) (Qiagen, Valencia, Calif.) was then added to a final concentration of 1 mM for the induction of expression at 25° C. for 6 h. Bacterial cells were collected by centrifugation, lyzed by Bugbuster (Novagen, Gibbstown, N.J.) and sonicated according to the manufacturer's instructions. Glutathione Sepharose 4B columns were equilibrated with phosphate buffered saline (PBS, pH 7.4) and lysate supernatant samples were loaded at a flow rate of approximately 1 mL/min. The columns were then washed with three columnvolumes of PBS. Finally, 50 mM Tris-HCl buffer (pH 7.4) containing 20 mM glutathione was used to elute the recombinant protein that was further purified with Mono Q 5/50 GL (GE Healthcare) with 20 mM Tris buffer (pH 6.8). Purified recombinant proteins were analyzed by SDS-PAGE (4-15% separation gel). Yields of rhTEM1-GST and rGST proteins were approximately 1 mg and 35 mg per liter of culture, respectively. Recombinant proteins were biotinylated using the EZ-Link Sulfo-NHS-Biotin-Reagents kit according to the manufacturer's instructions and dialyzed against PBS.

The full length hTEM1 cDNA was cloned into MluI/PacI-digested lentiviral plasmid vector pHRSIN-GFP to generate pHRSIN-TEM1 vector that expresses human TEM1 but not GFP. The corresponding lentivirus was generated by transient transfection of HEK293T cells with calcium phosphate. Conditioned medium containing viral vectors was harvested 24 and 48 hours after transfection, filtered (0.45 μm) and frozen at −80° C. until use. MS1, H5V and SKOV3 cells ($2\times10^4$ per 24-well plate) were transduced using 500

µL viral supernatants, and expression of hTEM1 was confirmed by RT-PCR (see FIG. 9 and methods), Western blot and flow cytometry analysis using a rabbit anti-TEM1 polyclonal antibody (kindly provided to GC by Morphotek, Inc, Malvern, Pa.).

Real-Time RT-PCR

Whole cell RNAs were prepared from cells using Trizol (Invitrogen, USA) according to the manufacturer's instructions. Total RNA was reverse-transcribed using Superscript First-Strand Synthesis Kit for RT-PCR (Invitrogen) under conditions described by the supplier. Primers, TaqMan probes and TaqMan assay reagents for human and mouse TEM1 and 18S were purchased from Applied Biosystems (ABI, USA). Human and murine TEM1 cDNA was quantified by real-time PCR on the ABI Prism 7900 Sequence Detection System (Applied Biosystems, Foster City, Calif.). PCR was performed according to manufacturer's instructions using ABI inventoried primer probes for human and mouse TEM1 and 18S as endogenous control as well as Taqman PCR core reagents. Amplification and detection was performed under the following conditions: one cycle of 50° C. for 2 min, one cycle of 95° C. for 10 min and 40 cycles each of 95° C. for 15 s and 60° C. for 1 min. Post-qRT-PCR calculations to analyze relative gene expression were performed by the comparative CT method ($2^{-\Delta\Delta CT}$ method).[42] Values were normalized with 18S as an endogenous control and MS1 cells was used as a calibrator, set as reference with a value of 1. All other test groups were set as being x-fold difference relative to the reference.

Flow Cytometry Analysis

Analysis of scFv expression by yeast was performed as previously described.[4] Binding of anti-TEM1 scFvs and biobodies to TEM1-expresser mammalian cells was evaluated using various human or murine cell lines expressing TEM1 endogenously (HEK-293T, MOV1 and 2H11) or stably transduced with pHRSIN-TEM1 (hTEM1-MS1, hTEM1-H5V and hTEM1-SKOV3). MS1 (murine endothelium), H5V (murine endothelium) and SKOV3 (human ovarian cancer) were used as negative or weakly positive control cell lines. Anti-TEM1 scFvs were preincubated for 30 min at RT with APC-anti-V5 at a ratio 1:1 and anti-TEM1 biobodies were preincubated with APC-labeled streptavidin at a ratio of 1:4. A non-relevant scFv was used as a negative control for binding.

Shuffling of Phage-Display scFv Library into Yeast

ScFvs initially cloned in the M13 phage display vector pComb3X (Scripps Research Institute, La Jolla, Calif.) were rescued by PCR from a phagemid DNA preparation. The primers were designed to bind to the original phage library scFv 5' and 3' end sequences, as well as to promote homologous recombination with the yeast-display vector pAGA2. Since the scFv constructs comprised light chain (kappa or lambda) variable regions ($V_L$'s) followed by a GS-rich linker peptide followed by γ heavy chain variable region sequences ($V_H$'s), forward primers annealed to the 5' ends of $V_L$'s and reverse primers annealed to the conserved 5' end of the $\gamma_{1,2,3,4}$ $C_H 1$ domain of the IgG heavy chain.

Primer Sequences for scFv Amplification from TTP Phage Library and Cloning by Homologous Recombination in pAGA2.

Forward primers:

| | |
|---|---|
| K1-F | Ggactggtggtggaggactggtggtggtggatctgtcgaca tccagatgacccagtctccatcc (SEQ ID NO: 5) |
| K24-F | Ggactggtggtggaggactggtggtggtggatctgtcgata ttgtgatgacycagtctccactc (SEQ ID NO: 6) |
| K3-F | ggttctggtggtggaggttctggtggtggtggatctgtcga aatwgtgwtgacrcagtctccagsc (SEQ ID NO: 7) |
| K5-F | ggttctggtggtggaggttctggtggtggtggatctgtcga aacgacactcacgcagtctccagca (SEQ ID NO: 8) |
| Lam1a | Ggactggtggtggaggactggtggtggtggatctgtccagt ctgtgctgactcagccaccctcg (SEQ ID NO: 9) |
| Lam1b | ggactggtggtggaggactggtggtggtggatctgtccagt ctgtgytgacgcagccgccctca (SEQ ID NO: 10) |
| Lam2 | ggactggtggtggaggactggtggtggtggatctgtccagt ctgccctgactcagcctccctcc (SEQ ID NO: 11) |
| Lam 3 | Ggactggtggtggaggactggtggtggtggatctgtctcct atgagctgactcagccaccctcag (SEQ ID NO: 12) |
| Lam 4 | Ggactggtggtggaggactggtggtggtggatctgtcctgc ctgtgctgactcaatcgccctctg (SEQ ID NO: 13) |
| Lam 6 | Ggttctggtggtggaggttctggtggtggtggatctgtcaa ttttatgctgactcagcccccactctg (SEQ ID NO: 14) |
| Lam 78 | Ggttctggtggtggaggttctggtggtggtggatctgtcca gactgtggtgacycaggagccmtcac (SEQ ID NO: 15) |
| Lam 9 | Ggactggtggtggaggactggtggtggtggatctgtccagc ctgtgctgactcagccaccactg (SEQ ID NO: 16) |
| Lam 10 | Ggactggtggtggaggactggtggtggtggatctgtccagg cagggcagactcagcagctctcgg (SEQ ID NO: 17) |

Reverse primer:

| | |
|---|---|
| 1234-B | gtcttcttcagaaataagcttttgttcggatccctcgaact ggccactagtgaccgatgg (SEQ ID NO: 18) |

PCR conditions for scFv amplification were: 94° C. for 5 min followed by 25 cycles of 94° C. 1 min, 55° C. 1 min and 72° C. 1 min, and a final extension of 7 min at 72° C. PCR products were then purified by electrophoresis using the Qiaquick Gel Extraction Kit (Invitrogen, Carlsbad, Calif.). pAGA2 vector for yeast display was linearized with NheI and XhoI and purified using the Qiaquick PCR Purification Kit (Invitrogen, Carlsbad, Calif.). EBY100 competent cells were prepared for electroporation according to the condition G (Table 2), and co-transfected with purified PCR products and pAGA2 linearized vector. Transfected yeast cells were finally expanded in SD-CAA mediumat 30° C. at 200 rpm until saturation. Ten-fold serial dilution of the transfected yeast were cultured on SD-CAA plates for calculation of the library's size.

The library's diversity and gap repair efficiency were evaluated by sequencing and flow cytometry analysis, respectively. In brief, 30 individual clones were randomly selected, induced in the medium SGRD-CAA, and assessed for scFv expression using the c-myc tag expressed only by yeast displaying scFv. Plasmid DNA was extracted from these clones using MasterPure Yeast DNA Purification Kit and scFv gene fragments were amplified for sequencing with primers flanking the gap repair sites. PCR amplification primers are: pAGA2-scFv-For: 5'-ccgtactctttgtcaacgac-3' (SEQ ID NO: 41) and pAGA2-scFv-Rev: 5'-ttaaagccttc-gagcgtccc-3'(SEQ ID NO: 42) Sequencing primers are: pAGA2-seq-For: 5'-gggaaggcaatgcaagga g-3' (SEQ ID NO:19) and pAGA2-seq-Rev: 5'-tgcgtacacgcgtctgtacag-3' (SEQ ID NO: 20).

Antibodies

Yeast-display scFv expression was detected with anti-c-myc mouse monoclonal antibody (mAb), 9E10 (Santa Cruz Biotechnology, Inc., Santa Cruz, Calif.) and Alexa488 F(ab')2 fragment of goat anti-mouse IgG (H+L) (488 anti-IgG) (Invitrogen, Carlsbad, Calif.) or PE-Cγ5 goat F(ab')2 anti-mouse IgG (H+L) (PE-Cu5 anti-IgG) (Cedarlane Laboratories Limited, Burlington, N.C.). Biotinylated antigen binding to yeast-display scFv was detected with goat anti-biotin-FITC (Abcam, Cambridge, Mass.) or streptavidin-PE (BD Pharmingen, San Jose, Calif.). ScFv binding to cell lines were detected with APC-conjugated anti-V5 mouse mAb (AbD Serotec, Raleigh, N.C.) (APC anti-V5) and scFv binding to plastic-immobilized antigen was detected by HRP-conjugated mouse anti-V5 mAb (AbD Serotec) (HRP-anti-V5). Biobody binding to TEM1-expresser cells was detected with APC-labeled streptavidin (eBioscience, San Diego, Calif.). Confocal microscopy was performed with anti-SV40 Tag mAb (Santa-Cruz Biotech, Santa Cruz, Calif.) detected by goat anti-mouse IgG1k-Alexa 488 mAb (488 anti-IgGlk) (Invitrogen, Carlsbad, Calif.), and rhodamine-labeled streptavidin (Invitrogen).

Identification of Anti-TEM1 scFv

The TTP yeast-display scFv library was first screened for anti-TEM1 scFv by magnetic and flow sorting as described. Anti-TEM1 yeast-display scFvs were then transformed into yeast-secreted scFv and screened by detection ELISA assays. Briefly, the library was magnetically enriched once for scFvs that bound to 20 nM of biotinylated rhTEM1-GST, twice for scFvs that bound to 6 nM of biotinylated rhTEM1-GST, then magnetically depleted for scFv that bound to 60 nM biotinylated rGST. Anti-TEM1 yeast-display scFvs were then flow sorted for c-myc/TEM1 double positive clones. Progressively decreasing concentrations of rhTEM1-GST were used during the screening (from 2 nM to 400 pM). DNA plasmids were extracted from yeast-display scFv that bound to 400 pM of rhTEM1-GST but not to 2 nM of rGST, and scFv fragments were amplified using primers allowing homologous recombination with the secretion vector p416-BCCP. The primers used were: Forward shuffling primer: 5'-ggttctggtggtggaggttctggtggtggtggatctg-3'(SEQ ID NO: 21); Reverse shuffling primer: 5'-gagaccgaggagagggttaggga-taggcttaccgtcgaccaagtcttcttcagaaataagctt-3' (SEQ ID NO: 22). ScFv fragments and linearized p416-BCCP were co-transfected into YVH10 by chemical transformation. Soluble scFv screening for specific binding to TEM1 was performed by ELISA with yeast supernatants of 470 random transformants in Maxisorp ELISA plates (Nunc, Rochester, N.Y.) coated with 0.8 μg/ml of rhTEM1-GST vs. rGST. Recombinant proteins were plastic-immobilized in carbonate-bicarbonate buffer 0.5 M, pH 9.6 (Fisher Scientific, Pittsburgh, Pa.) overnight (ON) at 4° C. Wells were then blocked with 5% dry milk in PBS (PBMS) (Biorad, Hercules, Calif.) for 2 hours at RT with gentle agitation and incubated with yeast supernatants diluted 1:1 with PBSM at RT for 1 h. After three washes with PBS supplemented with 0.05% Tween (PBST) (Biorad), scFv binding to immobilized proteins was detected with HRP anti-V5. Colorimetric signals were developed with TMB substrate solution (KPL, Inc., Gaithersburg, Md.), quenched with sulfuric acid (KPL, Inc) and read at 450 nm on a Fluoroskan Ascent FL (Thermo Fisher Scientific, Pittsburgh, Pa.). Approximately 50% of the colonies (232/470) gave a colorimetric signal higher than the average background plus 3 standard deviations. No cross-reactivity with rGST control protein was detected. Sequencing of 40 scFv identified five unique clones that were then produced and Ni-purified as previously described.

Measurement of scFv Affinity by ELISA

To assess scFv-78 affinity maxisorp ELISA plates were coated with rhTEM1-GST at two-fold decreasing concentrations from 0.4 to 0.05 μg/ml, in carbonate-bicarbonate buffer. After blocking with PBSM, wells were incubated with ten-fold serial dilutions of scFv-78, starting from 1 μM. ScFv binding to immobilized proteins was detected with HRP-conjugated mouse anti-V5 monoclonal antibody. Colorimetric signals were developed as previously described. The same procedure was followed for the other scFvs, but using 2 and 1 μg/ml of coated rhTEM1-GST and three-fold serial dilutions of scFv, starting at 2 μM.

Orthotopic Mouse Model of Ovarian Cancer

MOV-1 mouse ovarian cancer cell line was derived from an ovarian cancer that spontaneously arose in Tg-MISIIR-TAg mice. MOV-1 cell line expresses SV40 antigen and TEM1. To emulate ovarian cancer mouse ovarian cancer cells, MOV1 were orthotopically injected in the ovarian bursa of NOD-Scid-γc$^{null}$ (NSG) mice. Four month-old females were anesthetized according to the protocol approved by the University of Pennsylvania Institutional Animal Care and Use Committee (IACUC). A dorso-lateral incision on right caudal portion of the animal dorsum was made. The retroperitoneum was dissected to expose the left ovary using the forceps to grasp, retract, position, and secure the organ for injection. Five million MOV1 cells were injected in the ovarian bursa in a volume of 20 ml of PBS using an insulin syringe. Retroperitoneum wounds were closed, animals were administered antibiotics and fluids, and tumor growth was monitored by in vivo imaging.

Analysis of In Vivo Distribution of Anti-TEM1 Biobodies by Confocal Microscopy

Anti-TEM1 biobodies were injected IV 3 weeks after tumor cell implantation. Spleen, liver, kidney and ovaries were harvested 24 or 48 hours after biobody injection and preserved in frozen tissue matrix OCT compound (Tissue-Tek, Sakura Finetek USA). Slides of 5 mm thickness were cut from frozen sections, air dried 1 hr at RT and fixed by immersion in cold 100% acetone 5 min. After 2 washes in PBS, slides were blocked for endogenous biotin by pre-treatment with Avidin/Biotin Blocking solution (avidin-skim milk 0.001% in PBS). Biobody binding was detected with rhodamine-conjugated streptavidin. Tumor cells were detected with 2 μg/ml of SV40 Tag antibody for 30 min at RT followed by 1 μg/ml Alexa 488 goat anti-mouse IgG1K for 30 min at RT. Slides were incubated with 1:2000 diluted DAPI (Invitrogen) for 30 min at RT to visualize the nuclei. Fluorescent signals were acquired by confocal analysis (Zeiss LSM 510META NLO) at 63× magnification Epitope Mapping of scFv78 on Human TEM1

In order to further characterize scFv78, epitope mapping was performed using yeast display-peptides. The advantages of yeast-display peptides over synthesized peptides include 1) presence of post-translation modifications; 2) no need of purification; 3) entirely renewable; 4) cost-effectiveness. Our novel vector pAGA2 designed for yeast display enables cloning by homologous recombination and c-mcy tagging of the yeast-display peptides.

Six overlapping fragments of 200-220 bp were designed to cover the N-terminal extracellular domain of TEM1 (1.2 kb) that was used to isolate the recombinant antibody scFv78 from our novel yeast-display scFv library. The fragments were amplified by PCR and ligated by homologous recombination into pAGA2 vector. Epitope mapping was performed by flow cytometry biotinylated scFv78 (biobody) to probe the yeast-display TEM1-peptides. scFv78 biobody bound only to T6 peptide. The findings indicate that the binding site of scFv78 is situated between 324aa and 390aa.

Primers to amplify the small TEM1 fragments T1 (20-88aa), T2 (78-152aa), T3 (142-216aa), T4 (206-275aa), T5 (265-334aa) and T6 (324-390aa) are shown below according to the Genebank Access Number: NM_020404. Gene fragments of each small peptide were amplified by PCR and cloned into the yeast display vector pAGA2 via gap repair (homologous recombination) by co-transformation of the PCR fragments and the vector into yeast strain EBY100. Colonies with right gene insertion were induced to display the peptides on yeast surface and scFv78 biobody binding was evaluated by FACS using PE conjugated streptavidin.

Primers for the Six Small Peptides Cloning:

T1F: Ggt ggt gga ggt tct ggt ggt ggt gga tct Ccctgggctgctgagccc (SEQ ID NO: 23)

T1R: TTCTTCAGAAATAAGCTTTTGTTCGGATCCCTGCAGCCCGATCCA CAG (SEQ ID NO: 24)

T2F: Ggt ggt gga ggt tct ggt ggt ggt gga tct ccagccagccggctgctg (SEQ ID NO: 25)

T2R: TTCTTCAGAAATAAGCTTTTGTTCGGATCCGTCGACAGCCAGCGT GCAC (SEQ ID NO: 26)

T3F: Ggt ggt gga ggt tct ggt ggt ggt gga tct tggctggagggctcgtgc (SEQ ID NO: 27)

T3R: TTCTTCAGAAATAAGCTTTTGTTCGGATCCCTGCTTCACGCAGAGC AGAG (SEQ ID NO: 28)

T4F: Ggt ggt gga ggt tct ggt ggt ggt gga tct ggcaggggagcctctctg (SEQ ID NO: 29)

T4R: TTCTTCAGAAATAAGCTTTTGTTCGGATCCACAGGGGTCCTCGCA ACTG (SEQ ID NO: 30)

T5F: Ggt ggt gga ggt tct ggt ggt ggt gga tct gcagcagacgggcgcagttg (SEQ ID NO: 31)

T5R: TTCTTCAGAAATAAGCTTTTGTTCGGATCCCTCGAAGCCACCAACG TAG (SEQ ID NO: 32)

T6F: Ggt ggt gga ggt tct ggt ggt ggt gga tct cagatgtgtgtcaactacgttgg (SEQ ID NO: 33)

T6R: TTCTTCAGAAATAAGCTTTTGTTCGGATCCCGTCCAGCCACCGTTG AAG (SEQ ID NO: 34)

Amino Acids Sequences of the Six Small Peptides:

T1 (20-88aa):
(SEQ ID NO: 35)
PWAAEPRAACGPSSCYALFPRRRTFLEAWR
ACRELGGDLATPRTPEEAQRVDSLVGAGPASRLLWIGLQ

T2 (78-152aa):
(SEQ ID NO: 36)
PASRLLWIGLQRQARQCQLQRPLRGFTWTT
GDQDTAFTNWAQPASGGPCPAQRCVALEASGEHRWLEGSC
TLAVD

T3 (142-216aa):
(SEQ ID NO: 37)
WLEGSCTLAVDGYLCQFGFEGACPALQDE
AGQAGPAVYTTPFHLVSTEFEWLPFGSVAAVQCQAGRGASL
LCVKQ

T4 (206-275aa):
(SEQ ID NO: 38)
GRGASLLCVKQPEGGVGWSRAGPLCLGTG
CSPDNGGCEHECVEEVDGHVSCRCTEGFRLAADGRSCEDPC

T5 (265-334aa):
(SEQ ID NO: 39)
AADGRSCEDPCAQAPCEQQCEPGGPQGYS
CHCRLGFRPAEDDPHRCVDTDECQIAGVCQQMCVNYVGGF
E

T6 (324-390aa):
(SEQ ID NO: 40)
QMCVNYVGGFECYCSEGHELEADGISCSP
AGAMGAQASQDLGDELLDDGEDEEDEDEAWKAFNGGWT

Results

Example 1: Generation of Vectors for Yeast-Display and Yeast-Secretion of N-Terminal Biotinylated SCFV To overcome the loss of antigen specificity and/or affinity due to scFv transfer from cell surface display to secreted, two complementary vectors were developed, pAGA2 and p416 BCCP, which permit scFv to be displayed (FIG. 1a) or secreted (FIG. 1b) by the same expression system (S. cerevisiae) and through engineering at the same domain (N terminus), thus with similar post-translational modifications and conformation. In pAGA2 vector, scFv are fused at the N-terminus to Aga2, to permit display (FIG. 1). ScFv expressed by p416 BCCP are soluble and fused at the N-terminus to an enzymatically biotinylable domain (BCCP) separated from the scFv functional site by a flexible IgA hinge (FIG. 1). The presence of the IgA hinge minimizes conformational effects on scFv by biotinylated BCCP during its binding to immobilized or labeled streptavidin. The BCCP domain can be specifically biotinylated in vitro with a recombinant biotin ligase. To achieve in vivo biotinylation and secretion of biotinylated scFv (biobodies), mating of yeast-secreting scFv with yeast bearing biotin ligase has been developed. The vectors pAGA2 (FIG. 1c) and p416 BCCP (FIG. 1d) were derived from the shuttle vectors p414 GAL1 and p416 GAL1, allowing galactose-inducible expression in the presence of uracil or tryptophane, respectively, which minimizes growth bias.

Example 2: Optimization of Yeast Transformation

Figure 2:
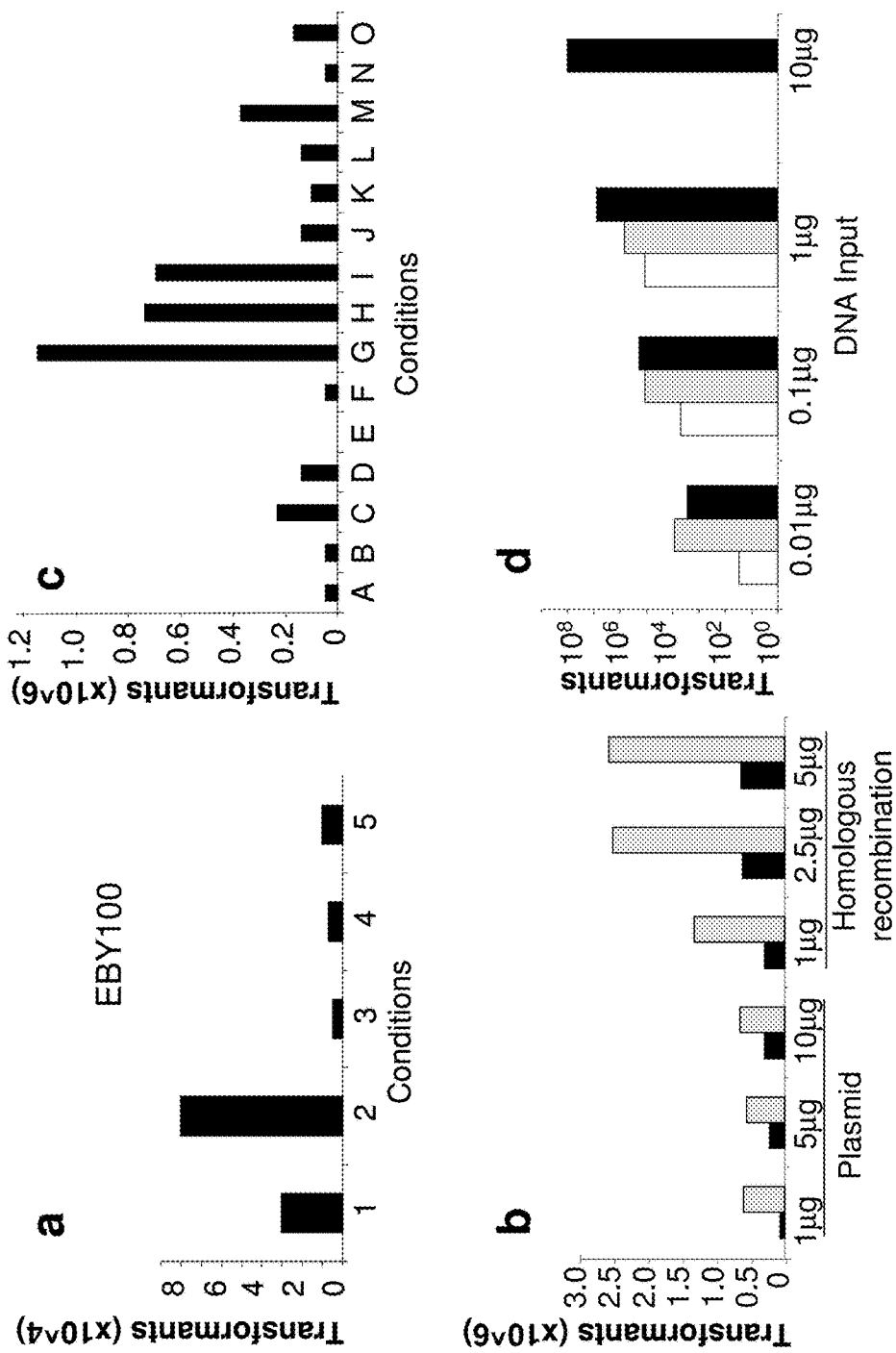
FIG. 2. Optimization of yeast transformations a-b Chemical transformations. Calibration of chemical transformation: a. EBY100 cells in log phase were treated by five different conditions described in Table 1. The number of transformants $\times 10^4$ per µg of plasmid DNA is plotted on the Y axis. b. Chemical transformation of EBY100 (black bars) vs. YVH10 (grey bars) with different concentrations of intact DNA plasmids (1 µg, 5 µg and 10 µg, as indicated) or of combinations of linearized plasmid and insert for homologous recombination (1 µg, 2.5 µg and 5 µg of linearized vector combined with 3-fold molar excess of scFv fragments, as indicated). The number of transformants $\times 10^6$ is plotted on the Y axis. c-d Electroporations. All experiments were performed in 0.2 cm cuvettes, in 50 ml volume, with settings of 1.5 kV, 25 mF and 200Ω. c. Calibrations: EBY100 cells in log phase were treated with fifteen different conditions (a-o) as described in Table 2. The number of transformants $\times 10^6$ per transformation with 1 µg of plasmid DNA is plotted on the Y axis. d. Electroporation of EBY100 in condition G, with different concentrations of linearized vector (white bars) or intact DNA plasmid (grey bars) or combination of linearized plasmid and insert (black bars) for homologous recombinations (as indicated). The number of transformants per transformation is plotted on the Y axis.
Figure 3:
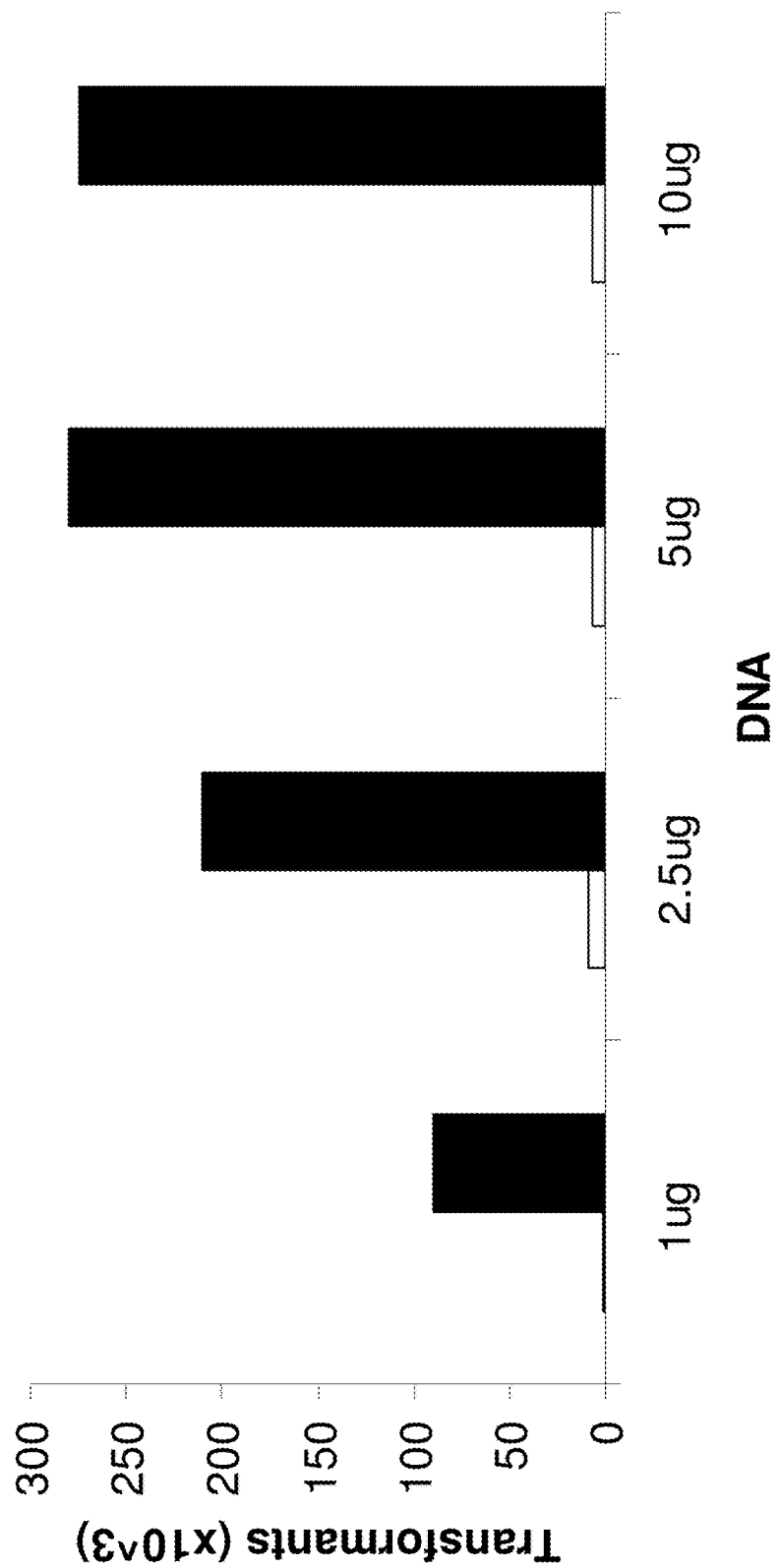
FIG. 3: Calibration of YVH10 electroporation conditions. YVH10 were electroporated with increasing amount of intact plasmid (white bars) or linearized plasmid and insert (black bars) to promote homologous recombinations. Electroporations were performed in 100 ul volume in 0.2 cm cuvette; the apparatus setting was 1.5 kV, 25 µF, and 200Ω.

Although chemical transformation with lithium acetate (LiAc) or electroporation can be used for yeast display library construction, it remains to date unclear whether these methods differ in transformation efficiency, especially for the strains used to display or secrete scFv (EBY100 and YVH10, respectively). Reported here is the first optimization of both methods. Table 1 shows the procedure for chemical competent cell preparation and transformation. Optimization was conducted in two steps, first by calibrating competent cell preparation and transformation, and then by optimizing DNA input. Condition 2 was best for chemical transformation (Table 1 and FIG. 2a) and was applied for the transformation of both EBV100 and YVH10 stains with intact plasmid or with combinations of linearized vector and insert for homologous combination (FIG. 2b). YVH10 chemical transformation yielded $10^6$ transformants per microgram of DNA by homologous recombination, which was unexpectedly higher than transformation with intact plasmid (FIG. 2b, gray bars). However, for EBY100 yeast the chemical transformation efficiency was low (FIG. 2b, black bars). Thus, we developed an alternate protocol for EBY100 transformation using electroporation (Table 2). While electroporation of YVH10 resulted in low yield and was not pursued (FIG. 3), condition G (Table 2 and FIG. 2c) gave the highest yield of transformants for EBV100, producing 1×10$^8$ transformants per electroporation with 10 μg of linearized vector and insert combined (FIG. 2d). Thus, both YVH10 and EBV100 yeast strains are more efficiently transformed by homologous recombination than by intact plasmids. YVH10 is best transformed by chemical transformation with heat shock, while EBV100 is best transformed by electroporation, and at levels compatible with generation of scFv libraries.

TABLE 1

| Conditions | Yeast resuspension | Yeast washes w/water & LiAc/TE | Yeast Incubation w/vector + insert | Heat Shock at 42° C. | Yeast recovery In YPED |
|---|---|---|---|---|---|
| 1 | Chill in ice | 4° C. | w/o DMSO | 30 min | 2 h |
| 2 | Room Temp. | 4° C. | w/o DMSO | 30 min | 2 h |
| 3 | Room Temp. | 4° C. | w/DMSO | 30 min | 2 h |
| 4 | Room Temp. | RT | w/o DMSO | 30 min | 2 h |
| 5 | Room Temp. | RT | w/DMSO | 15 min | 2 h |

TABLE 2

| conditions | [DTT] | buffer | [sorbitol] | shaking time | shaking P |
|---|---|---|---|---|---|
| A | 25 mM | | | 15 min | 30° C. |
| B | 25 mM | | | 30 min | 30° C. |
| C | 25 mM | 10 mM Tris | | 30 min | 30° C. |
| D | 25 mM | 20 mM Hepes | | 30 min | 30° C. |
| E | 25 mM | | 1M | 30 min | 30° C. |
| F | 25 mM | | 1M | 60 min | 4° C. |
| G | 25 mM | 20 mM Hepes | 0.6M | 30 min | 30° C. |
| H | 25 mM | 20 mM Hepes | 1M | 30 min | 30° C. |
| I | 25 mM | LiAc-TE | 0.6M | 30 min | 30° C. |
| J | 25 mM | LiAc-TE | 0.6M | 60 min | 4° C. |
| K | 25 mM | LiAc-TE | 1M | 30 min | 30° C. |
| L | 25 mM | LiAc-TE | 1M | 60 min | 4° C. |
| M | 25 mM | LiAc-TE | | 30 min | 30° C. |
| N | 25 mM | LiAc-TE | | 30 min | 4° C. |
| O | 25 mM | LiAc-TE | | 60 min | 4° C. |

Example 3: Construction and Validation of TTP Yeast-Display SCFV Library

Figure 4:
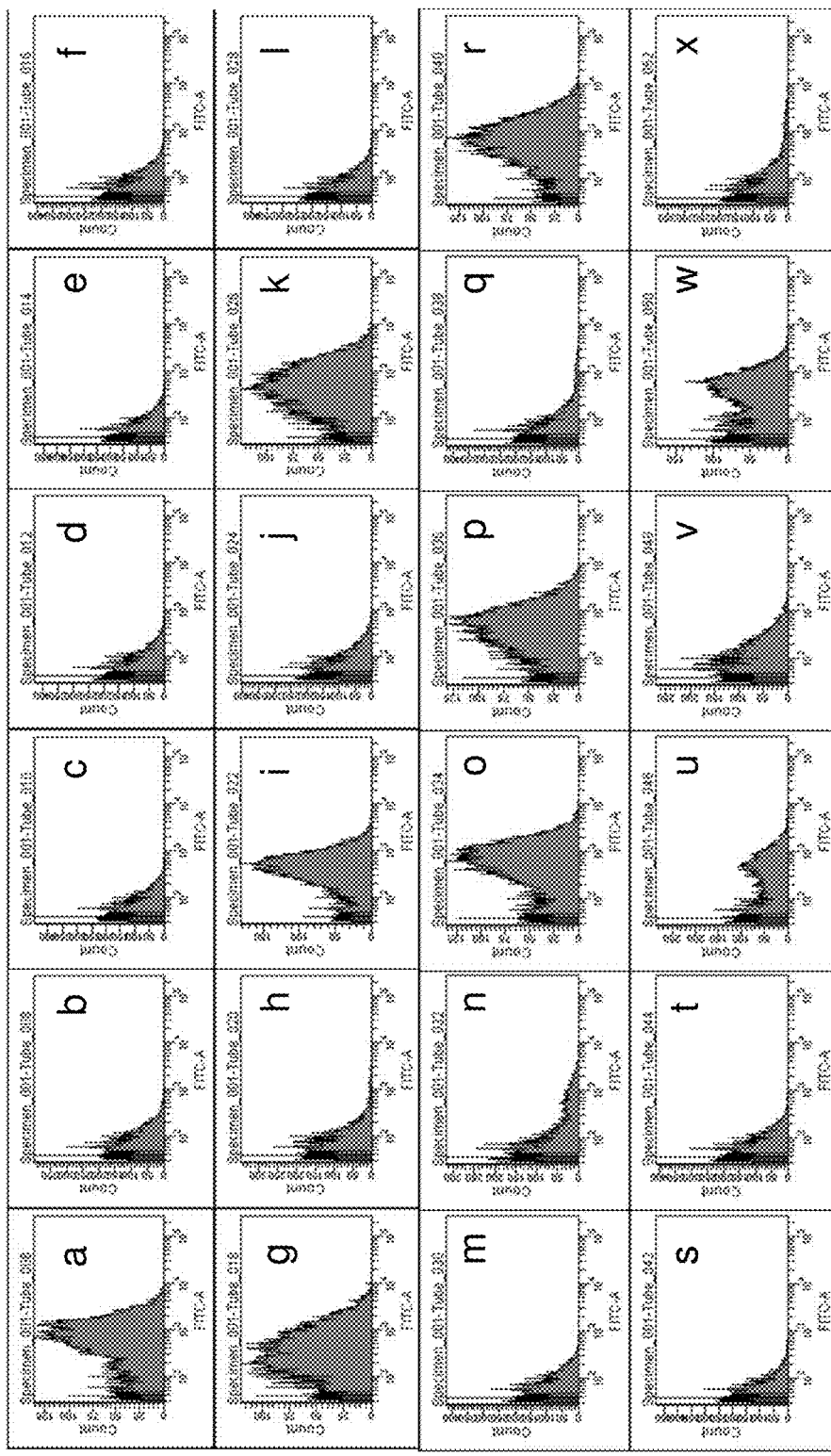
FIG. 4: Flow cytometry analysis of yeast-display scFv library. Yeast-display scFv were detected by anti-c-myc mAb followed up by 488-labeled anti-mIg.

The M13 phage-display human scFv library derived from a patient with thrombotic thrombocytopenic purpura (TTP), a coagulation system disorder caused by autoantibodies to the metalloprotease ADAMTS13, was previously reported. ScFv gene segments from the TTP phage display library were rescued by PCR from a phagemid DNA preparation, and co-transformed with pAGA2 linearized vector by electroporation in EBV100 yeast strain to allow homologous recombination and cell surface display. The diversity of the resulting yeast-display scFv library was validated by the sequencing of 20 randomly selected clones that demonstrated a gap repair rate of 95% (data not shown). Yeast-display scFv was assessed by flow cytometry through the detection of c-myc tag that is fused to the scFv C-terminus. Nine out of 24 randomly selected clones displayed scFvs on their surface after induction (FIG. 4 clones a,g,i,k,o,p,r,u,w), which was consistent with the expression ratio of phage and yeast libraries previously reported.

Example 4: Identification of Anti-TEM1 SCFV

TEM1 or endosialin was first described as a marker of tumor endothelial cells. Other studies showed that endosialin is highly expressed on pericytes and stroma cells related to tumor angiogenesis, proliferation, migration and metastasis. Recently, endosialin was described as both a tumor endothelial and an endothelial precursor cell marker with high expression in tumors and little or no expression in normal tissues. Therefore, targeting TEM1 with antibody or antibody-conjugated reagents such as an immunotoxin, isotope, or nanoparticles is a promising approach for both diagnosis and therapy. The TTP yeast-display library was enriched for scFv that bind to recombinant human TEM1-GST protein (rhTEM1-GST) first by magnetic and then by flow sortings and was depleted by magnetic sortings from scFv binding to control recombinant GST (rGST) protein, as previously described. Magnetic sorting is based on one parameter of selection only (capture of antigen-binding yeast), thereby providing a rapid means for robust enrichment of antigen-specific scFv. Flow sorting uses two parameters of selection, including antigen binding and recognition of c-myc tag on scFv displayed at the yeast cell surface, thereby further enriching for antigen-specific scFv while preventing the selection of yeast that bind to antigen directly through their coat. DNA was extracted from double-positive sorted yeast to amplify scFv sequences with primers allowing homologous recombination with p416 BCCP vector. Resulting transformants secreted scFv enriched for TEM1-specific binding.

Figure 5:
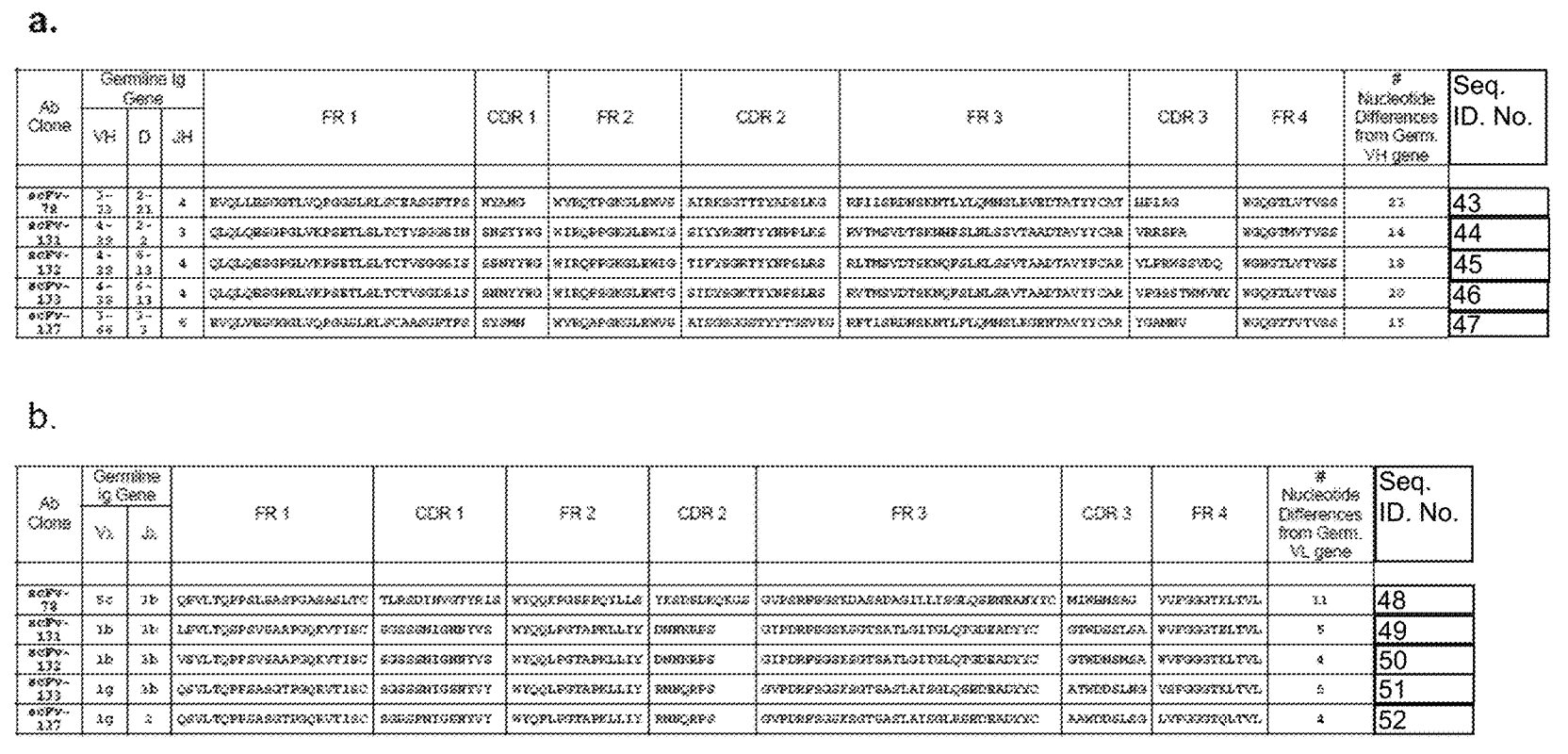

Four hundred and seventy yeast-secreting scFv were tested by ELISA for their ability to detect rhTEM1-GST. Almost 50% (232/470) of the soluble scFv bound to rhTEM1-GST but not to rGST. Anti-TEM1 soluble scFv were classified into two affinity categories: "high" when the optical density (OD) by detection ELISA was greater than 0.5, and "low" when lower than 0.5. Twenty scFv of each category were sequenced. The high OD group contained only one sequence (scFv-78) and three clones presented each one point mutation in the VL; #6 had a point mutation in FR1 that changed a serine in leucin; #8 a point mutation in FR3 changing a glycin in valine; #10 a point mutation in CDR2 changing a leucine in methionine. The low OD group included four different scFvs (scFv-131; scFv-132; scFv-133; scFv-137) (FIG. 5). Alignment of scFv heavy and light chain variable region sequences to a database of human immunoglobulin germline sequences (V Base Directory of Human V Gene Sequences) indicated that the heavy chain variable region sequences used VH3- and VH4-family-encoded gene products and showed extensive somatic mutation particularly in the CDR regions as though they evolved during an antigen-driven immune response (FIG. 5a). The light chain sequences used by all 5 anti-TEM1 scFv's were lambda and were minimally mutated from their most likely VL and JL germline genes (FIG. 5b).

Figure 6:
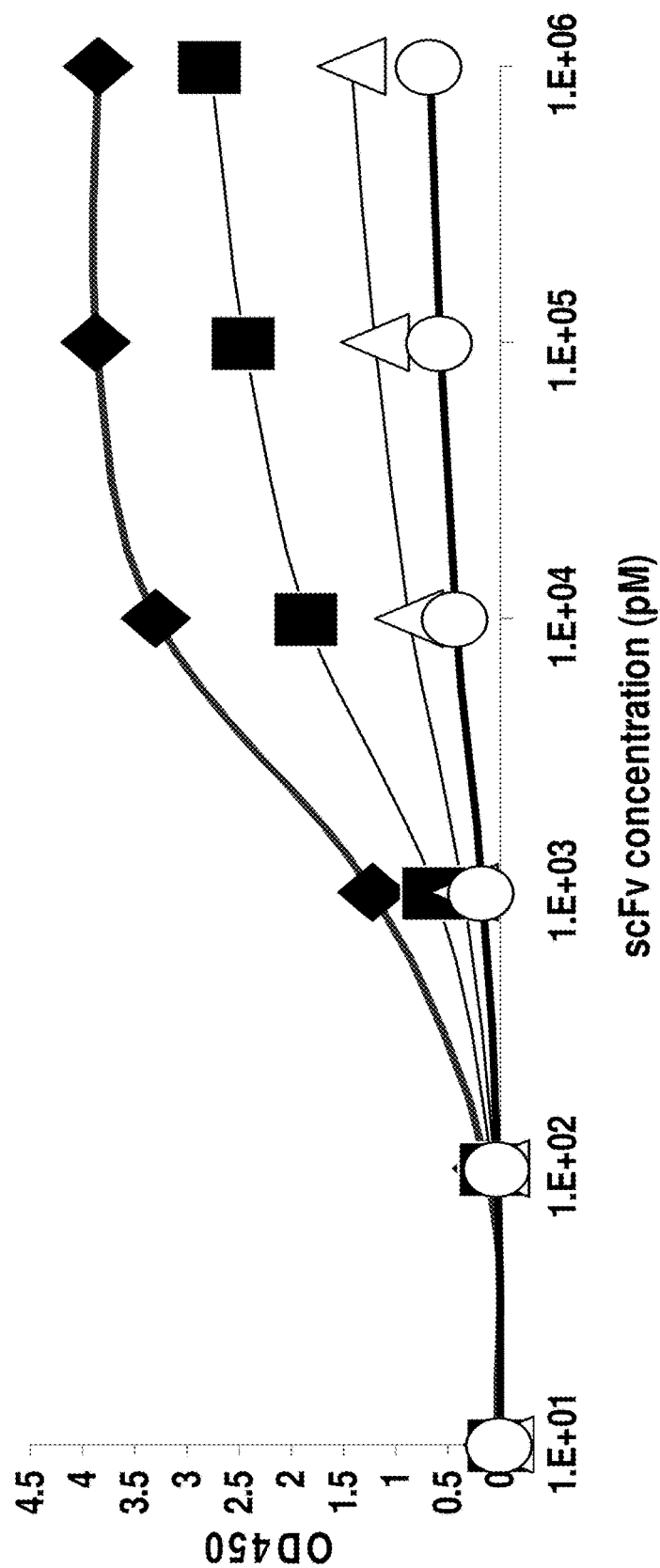
FIG. 6: Measurement of scFv-78 affinity by ELISA. Kd was calculated by the equation Kd=2[Ab']t−[Ab]t, where [Ab']t refers to the scFv concentration at $OD_{50}$ for the half concentration rhTEM1 coated wells while [Ab]t refers to the scFv concentration at OD50 for one concentration rhTEM1-GST coated wells. The calculated Kd for scFv-78 was 5.8 nM using antigen concentrations of 0.4 µg/ml (diamonds) and 0.2 µg/ml (squares), 4.5 nM using antigen concentrations of 0.2 µg/ml and 0.1 µg/ml (open triangles), or 2.8 nM using antigen concentration of 0.1 µg/ml and 0.05 µg/ml (open circles). ELISAs were performed in duplicate in two independent experiments. Lines are fitted using the antibody-antigen reaction equation.
Figure 7:
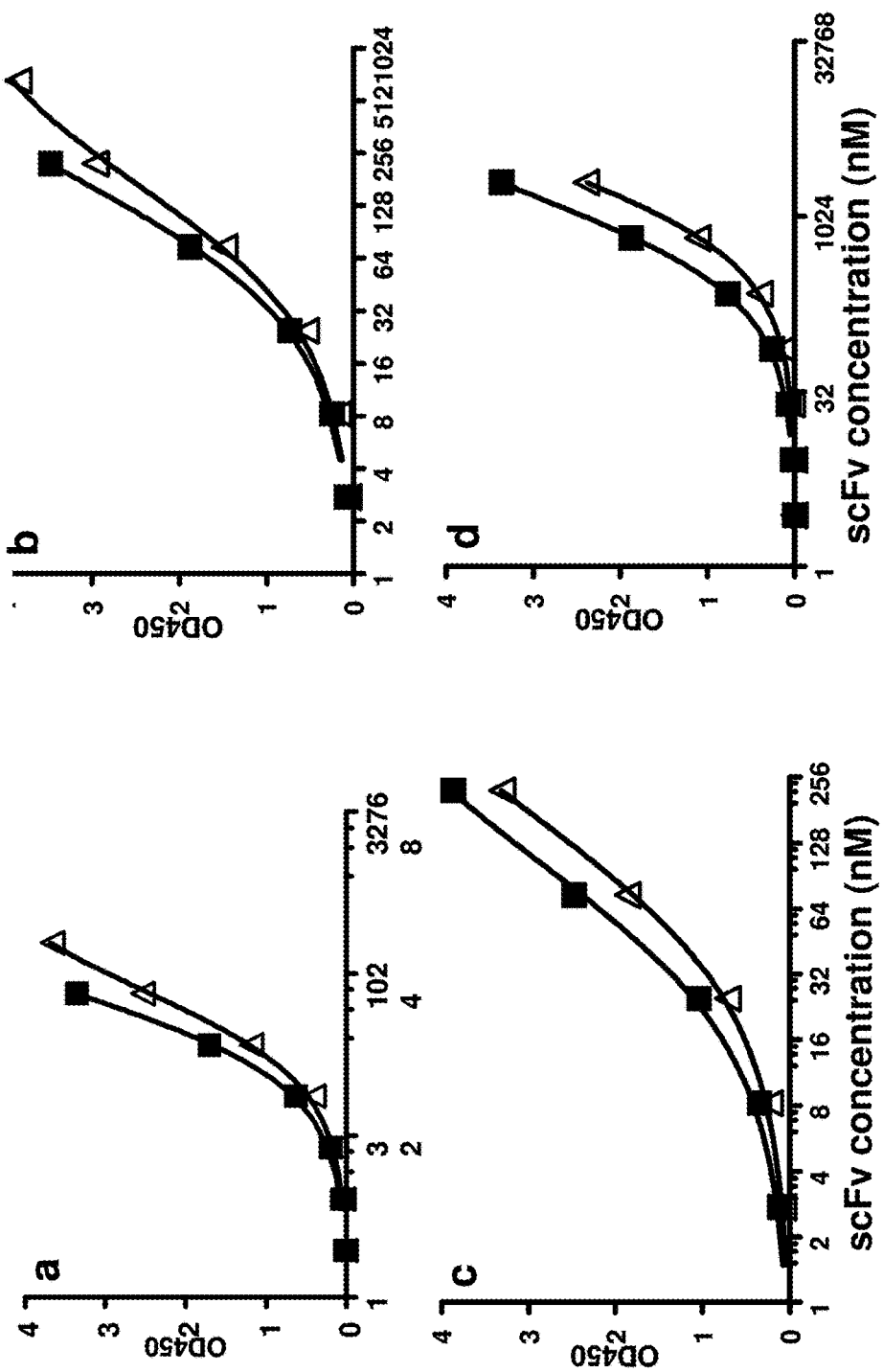
FIG. 7: Measurement of scFv-132; scFv-133; scFv-131 and scFv-137 affinities by ELISA. Kd was calculated by the equation Kd=2[Ab']t-[Ab]t, where [Ab']t refers to the scFv concentration at OD50 for the half concentration rhTEM1 coated wells while [Ab]t refers to the scFv concentration at OD50 for one concentration rhTEM1-coated wells. The calculated Kd's for each scFv are as follows: (a), 148 nM, scFv-132, (b), 218 nM, scFv-133, (c), 628 nM, scFv-131, and (d), 4.4 µM, scFv-137, using 2 µg/ml (squares) or 1 µg/ml (triangle) of rhTEM1. ELISAs were performed in duplicate in two independent experiments. Lines are fitted using the antibody-antigen reaction equation.

Example 5: Characterization and In Vitro Validation of Anti-TEM1 SCFVS and Biobodies ELISA provides a convenient way to evaluate the affinity of an antibody. Because a scFv has only one binding site for antigen, the affinity can be calculated by the equation of $Kd=2[Ab']_t-[Ab]_t$, derived from the Beatty's equation $K_{aff}=\frac{1}{2}(2[Ab']_t-[Ab]_t)$, where $[Ab']_t$ refers to scFv concentration at half the maximal OD ($OD_{50}$) for rhTEM1-GST-coated wells at half concentration, and [Ab] refers to scFv concentration at $OD_{50}$ for rhTEM1-GST-coated wells at whole concentration. The calculated Kd of the five anti-TEM1 scFvs with distinct sequences were 4.3+/−1.5 nM for scFv-78 (FIG. 6), 148 nM for scFv-132, 218 nM for scFv-133, 682 nM for scFv-131, and 4.4 μM for scFv-137, respectively (FIG. 7). $R^2$ of the curve fittings for all ELISAs were above 0.99. ScFv were then biotinylated on the BCCP site in N-termini by yeast mating with biotin ligase-bearing yeast to produce biobodies, as described by Scholler et al., and expressed at a yield of 10 mg per liter.

Figure 8:
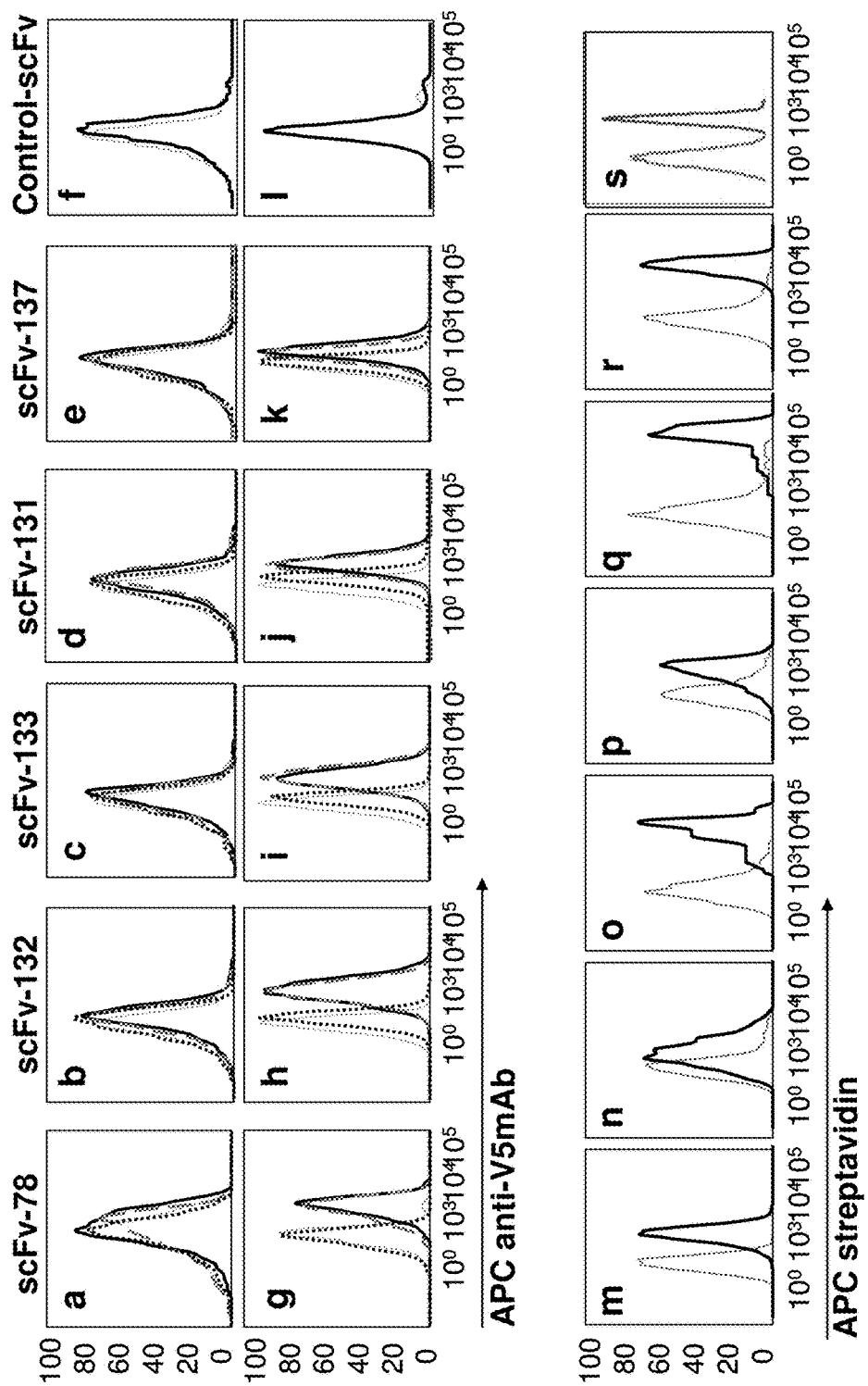
FIG. 8: Characterization of anti-TEM1 scFv binding. Wild type (a-f) and hTEM1-transfected (g-l) microvascular endothelial cells of murine pancreatic origin (Mile-Sven, MS1 cells, American Type Culture Collection, Manassas, Va.) were incubated with five different anti-TEM1 scFv (as indicated) at 10 nM for scFv-78 and at 1 µM for scFv-132, scFv-133, scFv-131, scFv-137, and an irrelevant control scFv. ScFv binding to cell surface was detected with APC-labeled anti-V5 (solid black line). Blocking conditions were performed in presence of 20 nM of rhTEM1-GST (small dotted line) or 100 nM of rGST control protein (dashed line) for scFv78 and 1 µM of rhTEM1-GST (small dotted line) or 1 µM of rGST control protein (dashed line) for scFv-131, -132, -133 and -137. As a negative control, cells were incubated with APC anti-V5 mAb only (grey line). m-s: Targeted biotinylated ScFv-78 (biobody-78) was incubated with TEM1-endogenous expresser embryonic kidney 293 cells (HEK293) (m); wild type heart endothelial mouse cells (H5V) (n); hTEM1-transfected H5V cells (o); wild type human ovarian cancer cells (SKOV3) (p); hTEM1-transfected SKOV3 cells (q); mouse TEM1-endogenous expresser endothelial cells (2H11) (r), and mouse TEM1-endogenous expresser ovarian cancer cells (MOV-1) (s). Biobody-78 binding was detected by 30 nM of APC-labeled streptavidin (black line). As a negative control, cells were incubated with APC-labeled streptavidin only (grey line).
Figure 9:
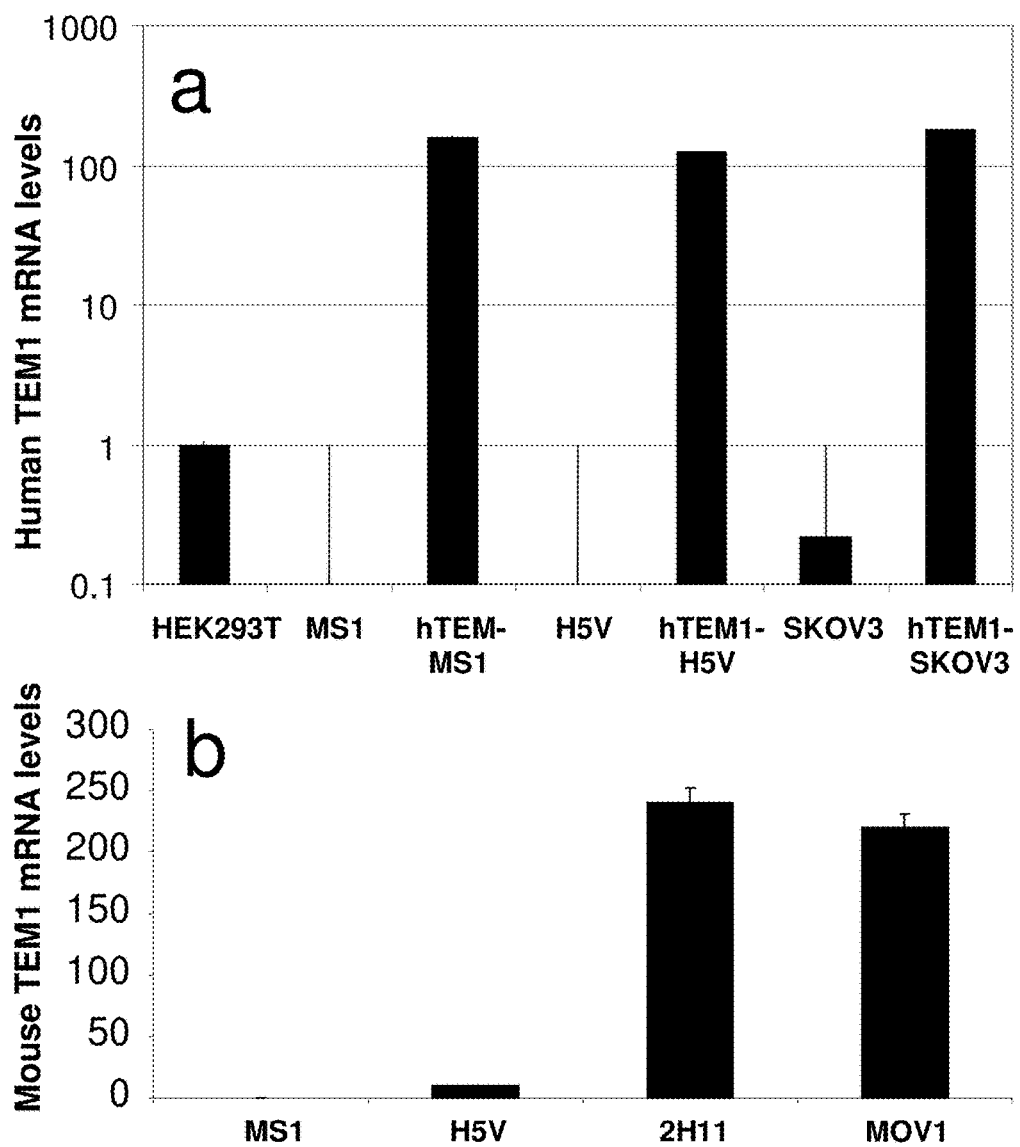
FIG. 9: TEM1 transcript expression levels in murine and human cell lines. a. Human endogenous and transduced expression levels of TEM1 were measured in wild type or hTEM-1-transduced murine endothelial cell lines MS1 and H5V cell lines, in human fibroblast cell line HEK293T and in human ovarian cancer cell line SKOV3 by qRT PCR, as indicated. b. Murine endogenous TEM1 transcript expression levels were measured in murine endothelial cell lines MS1, HSV, 2H11 and ovarian cancer cell line MOV1, as indicated.

Flow cytometry showed that all anti-TEM1 scFvs bound to the human TEM1-transfected mouse endothelial cell line hTEM1-MS1, but not to wild-type MS1 cells, and binding could be blocked with rhTEM1 but not with rGST (FIG. 8a-1). The remainder of the study was performed with the high affinity anti-TEM1 scFv-78 and low affinity scFv-137 after targeted biotinylation, resulting in biobody-78 and biobody-137, respectively. Biobody-78 strongly bound to cell lines transduced with human TEM1 (FIG. 8.o, q) and cells expressing high levels of endogenous human (FIG. 8.m) or mouse (FIG. 8.r, s) TEM1. Biobody-78 also bound to cell lines that express moderate levels of endogenous mouse or human TEM1, such as H5V (FIG. 8.n) and SKOV3 (FIG. 8.p), respectively. TEM1 mRNA expression level was verified by qRT-PCR in all cell lines (FIG. 9).

Example 6: In Vivo Validation of Anti-TEM1 scFVs

Figure 10:
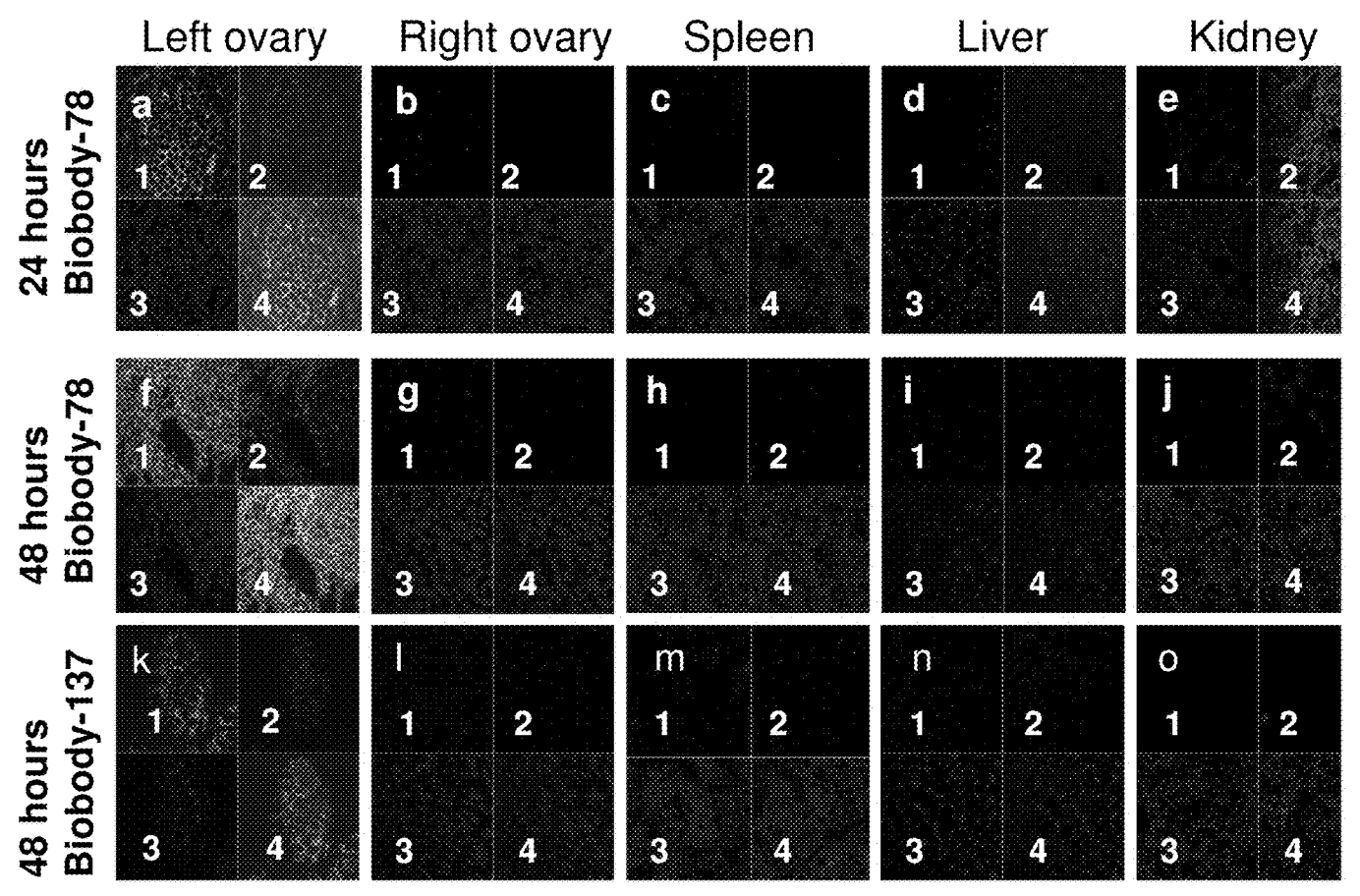

To test the ability of anti-TEM1 scFvs to recognize target in vivo, immunodeficient mice were transplanted orthotopically in the left ovarian bursae with MOV1 ovarian cancer cells, which express mouse TEM1 (FIG. 9B). Groups of mice were injected IV with a bolus of either the high-affinity biobody-78 or the low affinity biobody-137 (50 μg/mouse). Animals were euthanized after 24 or 48 hours, and spleens, livers, kidneys and ovaries were collected to monitor biobody distribution by confocal microscopy. Twenty-four hours after IV injection, anti-TEM1 biobody-78 was detected in kidneys but was cleared after 48 hours. Both anti-TEM1 biobody-78 and biobody-137 specifically localized to MOV1 cells implanted in the left ovaries after 48 hours but not in the contralateral normal ovaries or in the other normal mouse organs (FIG. 10).

Figure 11:
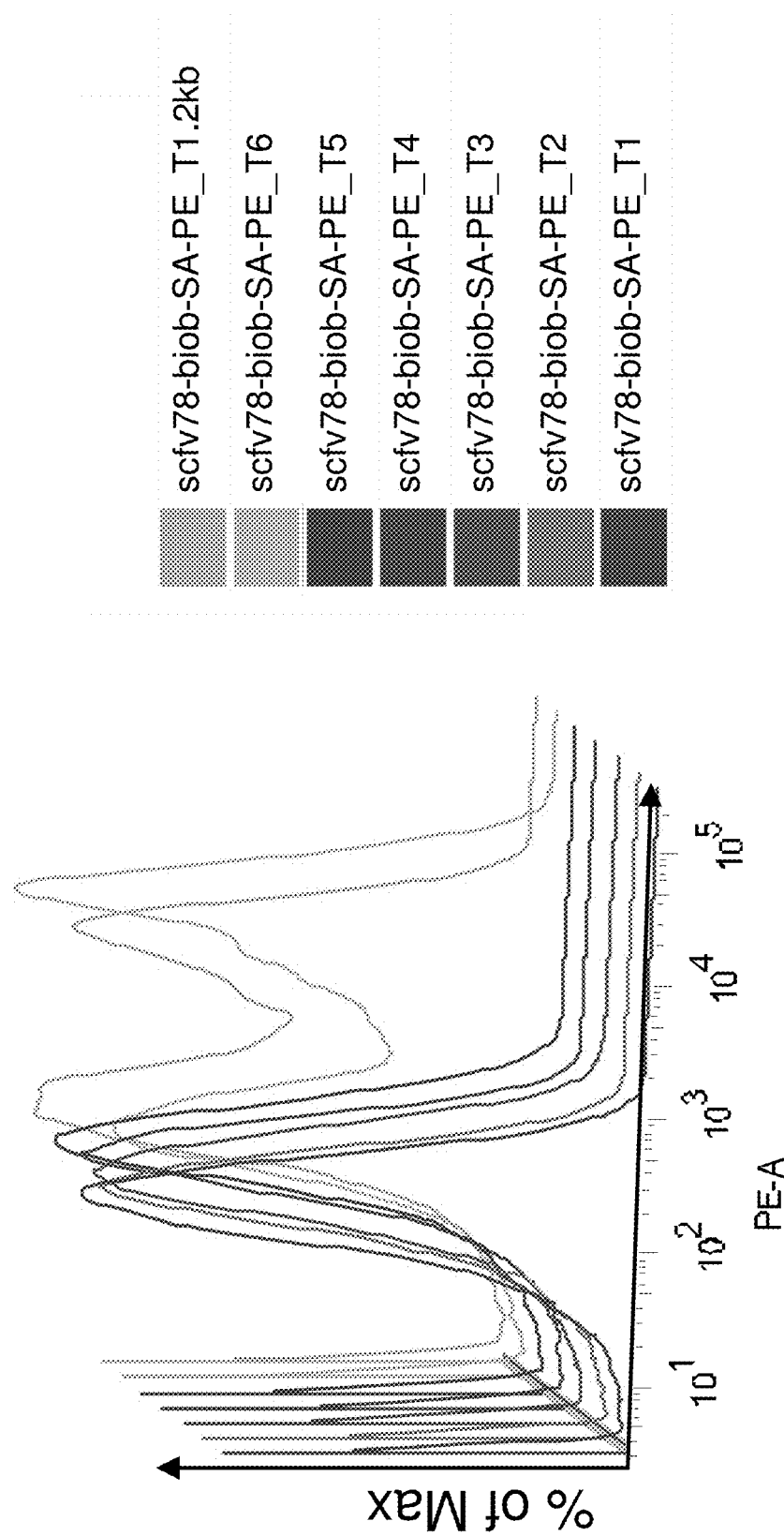
FIG. 11: scFv78-biob-SA-PE complex was prepared by pre-incubation of scFv78-biob and SA-PE for 30 min at 4 C with the ration of 4:1 and the concentration of SA-PE at 50 nM. Peptide displaying yeasts were incubated with scFv78-biob-SA-PE for 1 h at 4 C and scFv78-biob binding was evaluated by FACS.

Example 7: Epitope Mapping scFv78 biobody binds specifically onto the yeast displaying the small T6 peptide (324-390aa) and the control big N terminal peptide (20-390aa) (FIG. 11). The epitope on human TEM1 for scFv78 targeting is 324-390 amino acids residue, located in the middle of the extracellular domain (18-687 aa).

Example 8: Internalization of Anti-TEM1 Recombinant Antibody

Figure 12:
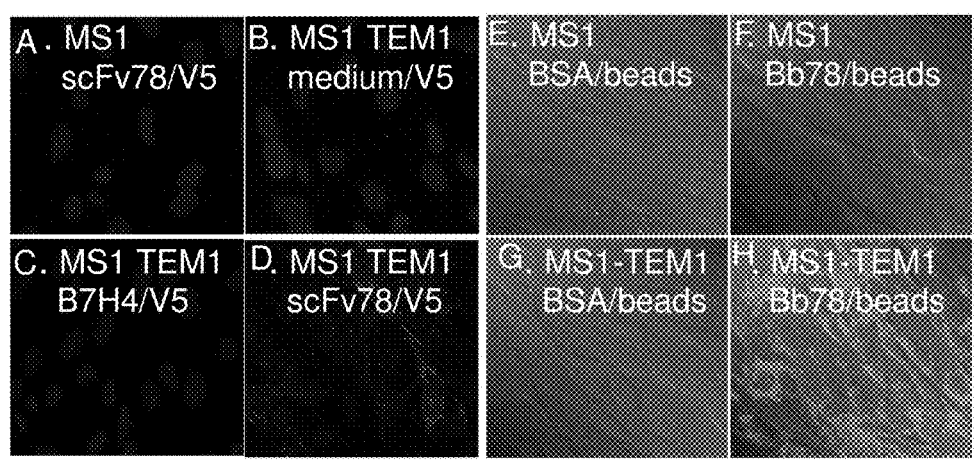
FIG. 12: Anti-TEM1 recombinant antibody internalizes in TEM1-expresser cells. MS1 endothelial cells, wild type (A,E,F) or transduced to express TEM1 (MS1-TEM1, B-D, G-H) were fixed, permeabilized, and incubated for 15 hours at 37° C. with anti-TEM1 scFv78 (A,D) or Biobody 78 (Bb78, F,H). Cells were then washed and incubated with alexa647-labeled anti-V5 antibody (A-D) or with dylight649-labeled beads (E-H). As negative controls, cells were incubated in medium only (B), or in medium supplemented with V5-tagged B7H4 protein (C) or BSA (E, G).

To assess the specific internalization of anti-TEM1 recombinant antibody in TEM1-expresser cells, we used two endothelial cell lines, the parental MS1 cell line and the TEM1-transduced MS1-TEM1 cell line. After fixation and permeabilization, cells were incubated in complete medium at 37° C. for 15 h with anti-TEM1 scFv78 detected by a fluorescently conjugated anti-V5 antibody (FIG. 12A,D) or with the site-specific biotinylated anti-TEM1 biobody78 bound to fluorescent beads (FIG. 12F,H). Fluorescent beads were obtained by incubating streptavidin-coated magnetic beads (Miltenyi) with a fluorescent conjugate (dylight648-labeled and biotinylated BSA). Confocal imaging demonstrated the specific internalization of both anti-TEM1 scFv78 and biobody78 in MS1-TEM1 cells (FIG. 12D, H), but not in wild type MS1 (fig. A, F). As negative controls, MS1 cells were incubated with BSA-coated fluorescent beads (FIG. 12E), and MS1-TEM1 cells were incubated in medium (FIG. 12B), with B7H4-V5 tag (FIG. 12C), or BSA-coated fluorescent beads (FIG. 12G).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of diagnosing the presence of a tumor or a cancer growth in a subject, said method comprising sampling a tissue sample isolated from said subject with a composition comprising an antibody or antigen-binding fragment thereof, wherein said antibody or antigen-binding fragment is specific for both the mouse and human form of an endosialin tumor endothelial marker 1 (TEM1) and binds to an epitope sequence as set forth in SEQ ID NO: 40, wherein the antibody or antigen-binding fragment comprises a heavy chain variable region comprising a CDR1 sequence of residues 31 to 35 of SEQ ID NO: 43; a CDR2 sequence of residues 50 to 65 of SEQ ID NO: 43; and a CDR3 sequence of residues 98 to 102 of SEQ ID NO: 43, and wherein the antibody or antigen-binding fragment comprises a light chain variable region comprising a CDR1 sequence of residues 23 to 36 of SEQ ID NO: 48; a CDR2 sequence of residues 52 to 62 of SEQ ID NO: 48; and a CDR3 sequence of residues 97 to 104 of SEQ ID NO: 48, whereby specific binding of said antibody or antigen-binding fragment to said tissue sample is indicative of the presence of a tumor or cancer growth in said subject.

2. The method of claim 1, further comprising a secondary reagent that specifically binds to said antibody or antigen-binding fragment but does not antagonize binding of said antibody or antigen-binding fragment to its target.

3. The method of claim 1, whereby said secondary reagent is a photoactivatable agent, a fluorophore, a radioisotope, a bioluminescent protein, a bioluminescent peptide, a fluorescent tag, a fluorescent protein, or a fluorescent peptide.

4. The method of claim 1, whereby said sampling comprises the step of analyzing said sample using a chromogenic immunological assay.

5. The method of claim 4, whereby said sampling comprises the step of analyzing said sample using microscopic imaging.

* * * * *

UNITED STATES PATENT AND TRADEMARK OFFICE
CERTIFICATE OF CORRECTION

| | | |
|---|---|---|
| PATENT NO. | : 10,160,809 B2 | Page 1 of 1 |
| APPLICATION NO. | : 15/411938 | |
| DATED | : December 25, 2018 | |
| INVENTOR(S) | : Nathalie Scholler et al. | |

It is certified that error appears in the above-identified patent and that said Letters Patent is hereby corrected as shown below:

In the Specification

Please replace Lines 15-22 in Column 1 with the following:
GOVERNMENT INTEREST STATEMENT
This invention was made with government support under grant number HL081012 awarded by the National Institutes of Health. The government has certain rights in the invention.

Signed and Sealed this
Ninth Day of November, 2021

Drew Hirshfeld
*Performing the Functions and Duties of the
Under Secretary of Commerce for Intellectual Property and
Director of the United States Patent and Trademark Office*

```
                        SEQUENCE LISTING

<160> NUMBER OF SEQ ID NOS: 52

<210> SEQ ID NO 1
<211> LENGTH: 392
<212> TYPE: DNA
<213> ORGANISM: Artificial Sequence
<220> FEATURE:
<223> OTHER INFORMATION: pAGA2 full insert sequence

<400> SEQUENCE: 1
agtgatgcag ttacttcgct gtttttcaat attttctgtt attgcttcag ttttagcaca      60
ggaactgaca actatatgcg agcaaatccc ctcaccaact ttagaatcga cgccgtactc     120
tttgtcaacg actactattt tggccaacgg gaaggcaatg caaggagttt ttgaatatta     180
caaatcagta acgtttgtca gtaattgcgg ttctcacccc tcaacaacta gcaaaggcag     240
ccccataaac acacagtatg ttttttgatta taaagatgac gataaaggtg gtggaggtgg     300
ttctggtggt ggaggttctg gtggtggtgg atctgctagc tgaattcctc gagggatccg     360
aacaaaagct tatttctgaa gaagacttgt aa                                    392

<210> SEQ ID NO 2
<211> LENGTH: 54
<212> TYPE: DNA
<213> ORGANISM: Artificial Sequence
```

<220> FEATURE:
<223> OTHER INFORMATION: recombination sequences for gap repair cloning

<400> SEQUENCE: 2
caaggagaaa aaactatatc tagaactagt gatgcagtta cttcgctgtt tttc        54

<210> SEQ ID NO 3
<211> LENGTH: 65
<212> TYPE: DNA
<213> ORGANISM: Artificial Sequence
<220> FEATURE:
<223> OTHER INFORMATION: recombination sequences for gap repair cloning

<400> SEQUENCE: 3
gtaagcgtga cataactaat tacatgactc gattacaagt cttcttcaga aataagcttt   60
tgttc                                                                65

<210> SEQ ID NO 4
<211> LENGTH: 510
<212> TYPE: DNA
<213> ORGANISM: Artificial Sequence
<220> FEATURE:
<223> OTHER INFORMATION: p416 BCCP full insert sequence

<400> SEQUENCE: 4
atgagatttc cttcaatttt tactgcagtt ttattcgcag catcctccgc attagctgct    60
ccagtcaaca ctacaacagg agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaaggggta   240
tctttggata aagatgtgta tggtttgaat gatattttg aagctcaaaa aattgaatgg    300
catgaaccat caacaccacc aactccaagt ccttctactc ctcctacacc ttcaccatca   360
gattataaag atgacgataa aggtggtgga ggtggttctg gtggtggagg ttctggtggt   420
ggtggatctg aattcgctag ctaagtcgac ggtaagccta tccctaaccc tctcctcggt   480
ctcgattcta cgcatcatca ccatcaccat                                    510

<210> SEQ ID NO 5
<211> LENGTH: 66
<212> TYPE: DNA
<213> ORGANISM: Artificial Sequence
<220> FEATURE:
<223> OTHER INFORMATION: K1-F forward primer

<400> SEQUENCE: 5
ggttctggtg gtggaggttc tggtggtggt ggatctgtcg acatccagat gacccagtct    60
ccatcc                                                               66

<210> SEQ ID NO 6
<211> LENGTH: 66
<212> TYPE: DNA
<213> ORGANISM: Artificial Sequence
<220> FEATURE:
<223> OTHER INFORMATION: forward primer

<400> SEQUENCE: 6
ggttctggtg gtggaggttc tggtggtggt ggatctgtcg atattgtgat gacycagtct    60
ccactc                                                               66

<210> SEQ ID NO 7
<211> LENGTH: 66
<212> TYPE: DNA
<213> ORGANISM: Artificial Sequence
<220> FEATURE:
<223> OTHER INFORMATION: forward primer

<400> SEQUENCE: 7
ggttctggtg gtggaggttc tggtggtggt ggatctgtcg aaatwgtgwt gacrcagtct    60 ccagsc                                                               66

<210> SEQ ID NO 8
<211> LENGTH: 66
<212> TYPE: DNA
<213> ORGANISM: Artificial Sequence
<220> FEATURE:
<223> OTHER INFORMATION: forward primer

<400> SEQUENCE: 8
ggttctggtg gtggaggttc tggtggtggt ggatctgtcg aaacgacact cacgcagtct    60
ccagca                                                               66

<210> SEQ ID NO 9
<211> LENGTH: 66
<212> TYPE: DNA
<213> ORGANISM: Artificial Sequence
<220> FEATURE:
<223> OTHER INFORMATION: forward primer

<400> SEQUENCE: 9
ggttctggtg gtggaggttc tggtggtggt ggatctgtcc agtctgtgct gactcagcca    60
ccctcg                                                               66

<210> SEQ ID NO 10
<211> LENGTH: 66
<212> TYPE: DNA
<213> ORGANISM: Artificial Sequence
<220> FEATURE:
<223> OTHER INFORMATION: forward primer

<400> SEQUENCE: 10
ggttctggtg gtggaggttc tggtggtggt ggatctgtcc agtctgtgyt gacgcagccg    60
ccctca                                                               66

<210> SEQ ID NO 11
<211> LENGTH: 66
<212> TYPE: DNA
<213> ORGANISM: Artificial Sequence
<220> FEATURE:
<223> OTHER INFORMATION: forward primer

<400> SEQUENCE: 11
ggttctggtg gtggaggttc tggtggtggt ggatctgtcc agtctgccct gactcagcct    60
ccctcc                                                               66

<210> SEQ ID NO 12
<211> LENGTH: 67
<212> TYPE: DNA
<213> ORGANISM: Artificial Sequence
<220> FEATURE:
<223> OTHER INFORMATION: forward primer -continued

<400> SEQUENCE: 12
ggttctggtg gtggaggttc tggtggtggt ggatctgtct cctatgagct gactcagcca    60
ccctcag    67

<210> SEQ ID NO 13
<211> LENGTH: 67
<212> TYPE: DNA
<213> ORGANISM: Artificial Sequence
<220> FEATURE:
<223> OTHER INFORMATION: forward primer

<400> SEQUENCE: 13
ggttctggtg gtggaggttc tggtggtggt ggatctgtcc tgcctgtgct gactcaatcg    60
ccctctg    67

<210> SEQ ID NO 14
<211> LENGTH: 67
<212> TYPE: DNA
<213> ORGANISM: Artificial Sequence
<220> FEATURE:
<223> OTHER INFORMATION: forward primer

<400> SEQUENCE: 14
ggttctggtg gtggaggttc tggtggtggt ggatctgtca attttatgct gactcagccc    60
cactctg    67

<210> SEQ ID NO 15
<211> LENGTH: 67
<212> TYPE: DNA
<213> ORGANISM: Artificial Sequence
<220> FEATURE:
<223> OTHER INFORMATION: forward primer

<400> SEQUENCE: 15
ggttctggtg gtggaggttc tggtggtggt ggatctgtcc agactgtggt gacycaggag    60 ccmtcac    67

<210> SEQ ID NO 16
<211> LENGTH: 67
<212> TYPE: DNA
<213> ORGANISM: Artificial Sequence
<220> FEATURE:
<223> OTHER INFORMATION: forward primer

<400> SEQUENCE: 16
ggttctggtg gtggaggttc tggtggtggt ggatctgtcc agcctgtgct gactcagcca    60
ccttctg    67

<210> SEQ ID NO 17
<211> LENGTH: 67
<212> TYPE: DNA
<213> ORGANISM: Artificial Sequence
<220> FEATURE:
<223> OTHER INFORMATION: forward primer

<400> SEQUENCE: 17
ggttctggtg gtggaggttc tggtggtggt ggatctgtcc aggcagggca gactcagcag    60
ctctcgg    67

```
<210> SEQ ID NO 18
<211> LENGTH: 60
<212> TYPE: DNA
<213> ORGANISM: Artificial Sequence
<220> FEATURE:
<223> OTHER INFORMATION: reverse primer

<400> SEQUENCE: 18
gtcttcttca gaaataagct tttgttcgga tccctcgaac tggccactag tgaccgatgg     60

<210> SEQ ID NO 19
<211> LENGTH: 18
<212> TYPE: DNA
<213> ORGANISM: Artificial Sequence
<220> FEATURE:
<223> OTHER INFORMATION: pAGA2-seq-Forward sequencing primer

<400> SEQUENCE: 19
gggaaggcaa tgcaagga                                                   18

<210> SEQ ID NO 20
<211> LENGTH: 21
<212> TYPE: DNA
<213> ORGANISM: Artificial Sequence
<220> FEATURE:
<223> OTHER INFORMATION: pAGA2-seq-Reverse sequencing primer

<400> SEQUENCE: 20
tgcgtacacg cgtctgtaca g                                               21

<210> SEQ ID NO 21
<211> LENGTH: 37
<212> TYPE: DNA
<213> ORGANISM: Artificial Sequence
<220> FEATURE:
<223> OTHER INFORMATION: scFv amplification forward shuffling primer

<400> SEQUENCE: 21
ggttctggtg gtggaggttc tggtggtggt ggatctg                              37

<210> SEQ ID NO 22
<211> LENGTH: 63
<212> TYPE: DNA
<213> ORGANISM: Artificial Sequence
<220> FEATURE:
<223> OTHER INFORMATION: scFv amplification reverse shuffling primer

<400> SEQUENCE: 22
gagaccgagg agagggttag ggataggctt accgtcgacc aagtcttctt cagaaataag     60
ctt                                                                   63

<210> SEQ ID NO 23
<211> LENGTH: 48
<212> TYPE: DNA
<213> ORGANISM: Artificial Sequence
<220> FEATURE:
<223> OTHER INFORMATION: Forward primer for T1 peptide cloning

<400> SEQUENCE: 23
ggtggtggag gttctggtgg tggtggatct ccctgggctg ctgagccc                  48

<210> SEQ ID NO 24
<211> LENGTH: 48
<212> TYPE: DNA
<213> ORGANISM: Artificial Sequence
```

```
<220> FEATURE:
<223> OTHER INFORMATION: Reverse primer for T1 peptide cloning

<400> SEQUENCE: 24
ttcttcagaa ataagctttt gttcggatcc ctgcagcccg atccacag            48

<210> SEQ ID NO 25
<211> LENGTH: 48
<212> TYPE: DNA
<213> ORGANISM: Artificial Sequence
<220> FEATURE:
<223> OTHER INFORMATION: Forward primer for T2 peptide cloning

<400> SEQUENCE: 25
ggtggtggag gttctggtgg tggtggatct ccagccagcc ggctgctg            48

<210> SEQ ID NO 26
<211> LENGTH: 49
<212> TYPE: DNA
<213> ORGANISM: Artificial Sequence
<220> FEATURE:
<223> OTHER INFORMATION: Reverse primer for T2 peptide cloning

<400> SEQUENCE: 26
ttcttcagaa ataagctttt gttcggatcc gtcgacagcc agcgtgcac           49

<210> SEQ ID NO 27
<211> LENGTH: 48
<212> TYPE: DNA
<213> ORGANISM: Artificial Sequence
<220> FEATURE:
<223> OTHER INFORMATION: Forward primer for T3 peptide cloning

<400> SEQUENCE: 27
ggtggtggag gttctggtgg tggtggatct tggctggagg gctcgtgc            48

<210> SEQ ID NO 28
<211> LENGTH: 50
<212> TYPE: DNA
<213> ORGANISM: Artificial Sequence
<220> FEATURE:
<223> OTHER INFORMATION: Reverse primer for T3 peptide cloning

<400> SEQUENCE: 28
ttcttcagaa ataagctttt gttcggatcc ctgcttcacg cagagcagag          50

<210> SEQ ID NO 29
<211> LENGTH: 48
<212> TYPE: DNA
<213> ORGANISM: Artificial Sequence
<220> FEATURE:
<223> OTHER INFORMATION: Forward primer for T4 peptide cloning

<400> SEQUENCE: 29
ggtggtggag gttctggtgg tggtggatct ggcaggggag cctctctg            48

<210> SEQ ID NO 30
<211> LENGTH: 49
<212> TYPE: DNA
<213> ORGANISM: Artificial Sequence
<220> FEATURE:
<223> OTHER INFORMATION: Reverse primer for T4 peptide cloning

<400> SEQUENCE: 30
ttcttcagaa ataagctttt gttcggatcc acaggggtcc tcgcaactg           49
```

```
<210> SEQ ID NO 31
<211> LENGTH: 50
<212> TYPE: DNA
<213> ORGANISM: Artificial Sequence
<220> FEATURE:
<223> OTHER INFORMATION: Forward primer for T5 peptide cloning

<400> SEQUENCE: 31
ggtggtggag gttctggtgg tggtggatct gcagcagacg ggcgcagttg              50

<210> SEQ ID NO 32
<211> LENGTH: 49
<212> TYPE: DNA
<213> ORGANISM: Artificial Sequence
<220> FEATURE:
<223> OTHER INFORMATION: Reverse primer for T5 peptide cloning

<400> SEQUENCE: 32
ttcttcagaa ataagctttt gttcggatcc ctcgaagcca ccaacgtag               49

<210> SEQ ID NO 33
<211> LENGTH: 53
<212> TYPE: DNA
<213> ORGANISM: Artificial Sequence
<220> FEATURE:
<223> OTHER INFORMATION: Forward primer for T6 peptide cloning

<400> SEQUENCE: 33
ggtggtggag gttctggtgg tggtggatct cagatgtgtg tcaactacgt tgg          53

<210> SEQ ID NO 34
<211> LENGTH: 49
<212> TYPE: DNA
<213> ORGANISM: Artificial Sequence
<220> FEATURE:
<223> OTHER INFORMATION: Reverse primer for T6 peptide cloning

<400> SEQUENCE: 34
ttcttcagaa ataagctttt gttcggatcc cgtccagcca ccgttgaag               49

<210> SEQ ID NO 35
<211> LENGTH: 69
<212> TYPE: PRT
<213> ORGANISM: Artificial Sequence
<220> FEATURE:
<223> OTHER INFORMATION: T1 peptide

<400> SEQUENCE: 35

Pro Trp Ala Ala Glu Pro Arg Ala Ala Cys Gly Pro Ser Ser Cys Tyr
1               5                   10                  15

Ala Leu Phe Pro Arg Arg Arg Thr Phe Leu Glu Ala Trp Arg Ala Cys
            20                  25                  30

Arg Glu Leu Gly Gly Asp Leu Ala Thr Pro Arg Thr Pro Glu Glu Ala
        35                  40                  45

Gln Arg Val Asp Ser Leu Val Gly Ala Gly Pro Ala Ser Arg Leu Leu
    50                  55                  60

Trp Ile Gly Leu Gln
65

<210> SEQ ID NO 36
<211> LENGTH: 75
<212> TYPE: PRT
<213> ORGANISM: Artificial Sequence
<220> FEATURE:
<223> OTHER INFORMATION: T2 peptide
```

<400> SEQUENCE: 36

Pro Ala Ser Arg Leu Leu Trp Ile Gly Leu Gln Arg Gln Ala Arg Gln
1               5                   10                  15

Cys Gln Leu Gln Arg Pro Leu Arg Gly Phe Thr Trp Thr Thr Gly Asp
                20                  25                  30

Gln Asp Thr Ala Phe Thr Asn Trp Ala Gln Pro Ala Ser Gly Gly Pro
            35                  40                  45

Cys Pro Ala Gln Arg Cys Val Ala Leu Glu Ala Ser Gly Glu His Arg
        50                  55                  60

Trp Leu Glu Gly Ser Cys Thr Leu Ala Val Asp
65                  70                  75

<210> SEQ ID NO 37
<211> LENGTH: 75
<212> TYPE: PRT
<213> ORGANISM: Artificial Sequence
<220> FEATURE:
<223> OTHER INFORMATION: T3 peptide

<400> SEQUENCE: 37

Trp Leu Glu Gly Ser Cys Thr Leu Ala Val Asp Gly Tyr Leu Cys Gln
1               5                   10                  15

Phe Gly Phe Glu Gly Ala Cys Pro Ala Leu Gln Asp Glu Ala Gly Gln
                20                  25                  30

Ala Gly Pro Ala Val Tyr Thr Thr Pro Phe His Leu Val Ser Thr Glu
            35                  40                  45

Phe Glu Trp Leu Pro Phe Gly Ser Val Ala Ala Val Gln Cys Gln Ala
        50                  55                  60

Gly Arg Gly Ala Ser Leu Leu Cys Val Lys Gln
65                  70                  75

<210> SEQ ID NO 38
<211> LENGTH: 70
<212> TYPE: PRT
<213> ORGANISM: Artificial Sequence
<220> FEATURE:
<223> OTHER INFORMATION: T4 peptide

<400> SEQUENCE: 38

Gly Arg Gly Ala Ser Leu Leu Cys Val Lys Gln Pro Glu Gly Gly Val
1               5                   10                  15

Gly Trp Ser Arg Ala Gly Pro Leu Cys Leu Gly Thr Gly Cys Ser Pro
                20                  25                  30

Asp Asn Gly Gly Cys Glu His Glu Cys Val Glu Val Asp Gly His
            35                  40                  45

Val Ser Cys Arg Cys Thr Glu Gly Phe Arg Leu Ala Ala Asp Gly Arg
        50                  55                  60

Ser Cys Glu Asp Pro Cys
65                  70

<210> SEQ ID NO 39
<211> LENGTH: 70
<212> TYPE: PRT
<213> ORGANISM: Artificial Sequence
<220> FEATURE:
<223> OTHER INFORMATION: T5 peptide

<400> SEQUENCE: 39

Ala Ala Asp Gly Arg Ser Cys Glu Asp Pro Cys Ala Gln Ala Pro Cys
1               5                   10                  15

Glu Gln Gln Cys Glu Pro Gly Gly Pro Gln Gly Tyr Ser Cys His Cys
            20                  25                  30

Arg Leu Gly Phe Arg Pro Ala Glu Asp Pro His Arg Cys Val Asp
        35                  40                  45

Thr Asp Glu Cys Gln Ile Ala Gly Val Cys Gln Gln Met Cys Val Asn
    50                  55                  60

Tyr Val Gly Gly Phe Glu
65                  70

<210> SEQ ID NO 40
<211> LENGTH: 67
<212> TYPE: PRT
<213> ORGANISM: Artificial Sequence
<220> FEATURE:
<223> OTHER INFORMATION: T6 peptide

<400> SEQUENCE: 40

Gln Met Cys Val Asn Tyr Val Gly Gly Phe Glu Cys Tyr Cys Ser Glu
1               5                   10                  15

Gly His Glu Leu Glu Ala Asp Gly Ile Ser Cys Ser Pro Ala Gly Ala
            20                  25                  30

Met Gly Ala Gln Ala Ser Gln Asp Leu Gly Asp Glu Leu Leu Asp Asp
        35                  40                  45

Gly Glu Asp Glu Glu Asp Glu Asp Glu Ala Trp Lys Ala Phe Asn Gly
    50                  55                  60

Gly Trp Thr
65

<210> SEQ ID NO 41
<211> LENGTH: 20
<212> TYPE: DNA
<213> ORGANISM: Artificial Sequence
<220> FEATURE:
<223> OTHER INFORMATION: Forward pAGA2-scFv amplification primers

<400> SEQUENCE: 41
ccgtactctt tgtcaacgac                                            20

<210> SEQ ID NO 42
<211> LENGTH: 20
<212> TYPE: DNA
<213> ORGANISM: Artificial Sequence
<220> FEATURE:
<223> OTHER INFORMATION: Reverse pAGA2-scFv amplification primers

<400> SEQUENCE: 42
ttaaagcctt cgagcgtccc                                            20

<210> SEQ ID NO 43
<211> LENGTH: 113
<212> TYPE: PRT
<213> ORGANISM: Artificial Sequence
<220> FEATURE:
<223> OTHER INFORMATION: Phage Display

<400> SEQUENCE: 43

```
Glu Val Gln Leu Leu Glu Ser Gly Gly Thr Leu Val Gln Pro Gly Gly
1               5                   10                  15
Ser Leu Arg Leu Ser Cys Glu Ala Ser Gly Phe Thr Phe Ser Asn Tyr
            20                  25                  30
Ala Met Gly Trp Val Arg Gln Thr Pro Gly Lys Gly Leu Ala Trp Val
        35                  40                  45
Ser Ala Ile Arg Lys Ser Gly Thr Thr Thr Tyr Ala Asp Ser Leu Lys
    50                  55                  60
Gly Arg Phe Ile Ile Ser Arg Asp Asn Ser Lys Asn Thr Leu Tyr Leu
65                  70                  75                  80
Gln Met Asn Ser Leu Arg Val Glu Asp Thr Ala Thr Tyr Tyr Cys Ala
                85                  90                  95
Thr His Pro Ile Ala Gly Trp Gly Gln Gly Thr Leu Val Thr Val Ser
            100                 105                 110
Ser
```

<210> SEQ ID NO 44
<211> LENGTH: 116
<212> TYPE: PRT
<213> ORGANISM: Artificial Sequence
<220> FEATURE:
<223> OTHER INFORMATION: Phage Display

<400> SEQUENCE: 44

```
Gln Leu Gln Leu Gln Glu Ser Gly Pro Gly Leu Val Lys Pro Ser Glu
1               5                   10                  15
Thr Leu Ser Leu Thr Gln Thr Val Ser Gly Gly Ser Ile Asn Ser Asn
            20                  25                  30
Ser Tyr Tyr Trp Gly Trp Ile Arg Gln Pro Pro Gly Lys Gly Leu Glu
        35                  40                  45
Trp Ile Gly Ser Ile Tyr Tyr Arg Gly Asn Thr Tyr Tyr Asn Pro Pro
    50                  55                  60
Leu Lys Ser Arg Val Thr Met Ser Val Asp Thr Ser Lys Asn His Pro
65                  70                  75                  80
Ser Leu Asn Leu Ser Ser Val Thr Ala Ala Asp Thr Ala Val Tyr Tyr
                85                  90                  95
Cys Ala Arg Val Arg Arg Ser Pro Ala Trp Gly Gln Gly Thr Met Val
            100                 105                 110
Thr Val Ser Ser
        115
```

<210> SEQ ID NO 45
<211> LENGTH: 120
<212> TYPE: PRT
<213> ORGANISM: Artificial Sequence
<220> FEATURE:
<223> OTHER INFORMATION: Phage Display

<400> SEQUENCE: 45

```
Gln Leu Gln Leu Gln Asx Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Asn Tyr Tyr Trp Gly Trp Ile Arg Gln Pro Pro Gly Lys Gly Leu Glu
        35                  40                  45
```

Trp Ile Gly Thr Ile Phe Tyr Ser Gly Arg Thr Tyr Tyr Asn Pro Ser
        50                  55                  60

Leu Arg Ser Arg Leu Thr Met Ser Val Asp Thr Ser Lys Asn Gln Pro
65                  70                  75                  80

Ser Leu Lys Leu Ser Ser Val Thr Ala Ala Asp Thr Ala Val Tyr Phe
                85                  90                  95

Cys Ala Arg Val Leu Pro Arg Trp Ser Ser Val Asp Gln Trp Gly His
                100                 105                 110

Gly Thr Leu Val Thr Val Ser Ser
            115                 120

<210> SEQ ID NO 46
<211> LENGTH: 121
<212> TYPE: PRT
<213> ORGANISM: Artificial Sequence
<220> FEATURE:
<223> OTHER INFORMATION: Phage Display

<400> SEQUENCE: 46

Gln Leu Gln Leu Gln Glu Ser Gly Pro Arg Leu Val Lys Pro Ser Glu
1               5                   10                  15

Thr Leu Ser Leu Thr Cys Thr Val Ser Gly Asp Ser Ile Ser Ser Asn
                20                  25                  30

Asn Tyr Tyr Trp Gly Trp Ile Arg Gln Pro Ser Gly Lys Gly Leu Glu
            35                  40                  45

Trp Ile Gly Ser Ile Asp Tyr Ser Gly Lys Thr Tyr Tyr Asn Pro Ser
        50                  55                  60

Leu Glu Ser Arg Val Thr Met Ser Val Asp Thr Ser Lys Asn Gln Phe
65                  70                  75                  80

Ser Leu Asn Leu Ser Ala Val Thr Ala Ala Asp Thr Ala Val Tyr Tyr
                85                  90                  95

Cys Ala Arg Val Pro Gly Ser Ser Thr Trp Met Val Asn Tyr Trp Gly
                100                 105                 110

Gln Gly Thr Leu Val Thr Val Ser Ser
            115                 120

<210> SEQ ID NO 47
<211> LENGTH: 114
<212> TYPE: PRT
<213> ORGANISM: Artificial Sequence
<220> FEATURE:
<223> OTHER INFORMATION: Phage Display

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Pro Thr Phe Ser Ser Tyr
                20                  25                  30

Ser Met Asn Trp Val Arg Gln Ala Pro Gly Lys Gly Leu Glu Trp Val
            35                  40                  45

Ser Ala Ile Ser Gly Ser Gly Ser Thr Tyr Tyr Thr Gly Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Gly Glu Asn Thr Ala Val Tyr Cys Ala
                85                  90                  95

Arg Tyr Gly Ala Met Asn Val Trp Gly Gln Gly Thr Thr Val Thr Val
                100                 105                 110

Ser Ser

<210> SEQ ID NO 48
<211> LENGTH: 116
<212> TYPE: PRT
<213> ORGANISM: Artificial Sequence
<220> FEATURE:
<223> OTHER INFORMATION: Phage Display

<400> SEQUENCE: 48

Gln Pro Val Leu Thr Gln Pro Pro Ser Leu Ser Ala Ser Pro Gly Ala
1               5                   10                  15

Ser Ala Ser Leu Thr Cys Thr Leu Arg Ser Asp Ile Asn Val Gly Thr
                20                  25                  30

Tyr Arg Ile Ser Trp Tyr Gln Gln Lys Pro Gly Ser Pro Pro Gln Tyr
            35                  40                  45

Leu Leu Ser Tyr Lys Ser Asp Ser Asp Lys Gln Lys Gly Ser Gly Val
50                  55                  60

Pro Ser Arg Phe Ser Gly Ser Lys Asp Ala Ser Ala Asp Ala Gly Ile
65                  70                  75                  80

Leu Leu Ile Ser Gly Leu Gln Ser Glu Asn Glu Ala Asn Tyr Tyr Cys
                85                  90                  95

Met Ile Trp His Asn Ser Ala Gly Val Val Phe Gly Gly Gly Thr Lys
                100                 105                 110

Leu Thr Val Leu
            115

<210> SEQ ID NO 49
<211> LENGTH: 110
<212> TYPE: PRT
<213> ORGANISM: Artificial Sequence
<220> FEATURE:
<223> OTHER INFORMATION: Phage Display

<400> SEQUENCE: 49

Leu Pro Val Leu Thr Gln Ser Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Pro Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Glu Leu Thr Val Leu
            100                 105                 110

<210> SEQ ID NO 50
<211> LENGTH: 110
<212> TYPE: PRT
<213> ORGANISM: Artificial Sequence
<220> FEATURE:
<223> OTHER INFORMATION: Phage Display

<400> SEQUENCE: 50

Asx Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Met
                85                  90                  95

Ser Ala Trp Val Phe Gly Gly Gly Thr Lys Leu Thr Val Leu
            100                 105                 110

<210> SEQ ID NO 51
<211> LENGTH: 110
<212> TYPE: PRT
<213> ORGANISM: Artificial Sequence
<220> FEATURE:
<223> OTHER INFORMATION: Phage Display

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Glu Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Val Ser Phe Gly Gly Gly Thr Lys Leu Thr Val Leu
            100                 105                 110

<210> SEQ ID NO 52
<211> LENGTH: 110
<212> TYPE: PRT
<213> ORGANISM: Artificial Sequence
<220> FEATURE:
<223> OTHER INFORMATION: Phage Display

<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Arg Ser Pro Asn Ile Gly Ser Asn
            20                  25                  30

Tyr Val Tyr Trp Tyr Gln Phe Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

-continued

```
Ser Glu Asp Glu Ala Asp Tyr Tyr Cys Ala Ala Trp Asp Asp Ser Leu
                85                  90                  95

Ser Gly Leu Val Phe Gly Gly Gly Thr Gln Leu Thr Val Leu
            100                 105                 110
```